(12) United States Patent
Qian et al.

(10) Patent No.: US 12,162,885 B2
(45) Date of Patent: Dec. 10, 2024

(54) CRYSTAL FORM OF XEVINAPANT FOR TREATING LA SCCHN

(71) Applicant: CRYSTAL PHARMACEUTICAL (SUZHOU) CO., LTD., Jiangsu (CN)

(72) Inventors: Jiale Qian, Suzhou (CN); Chunxiang Huang, Suzhou (CN); Liping Meng, Suzhou (CN)

(73) Assignee: CRYSTAL PHARMACEUTICAL (SUZHOU) CO., LTD., Suzhou (CN)

( * ) Notice: Subject to any disclaimer, the term of this patent is extended or adjusted under 35 U.S.C. 154(b) by 0 days.

(21) Appl. No.: 18/658,960

(22) Filed: May 8, 2024

(65) Prior Publication Data
US 2024/0287085 A1    Aug. 29, 2024

Related U.S. Application Data

(63) Continuation of application No. PCT/CN2023/108830, filed on Jul. 24, 2023.

(30) Foreign Application Priority Data

Jul. 29, 2022 (CN) .......................... 202210906912.X
Nov. 4, 2022 (CN) .......................... 202211375174.7

(51) Int. Cl.
A61K 31/395 (2006.01)
A61K 31/407 (2006.01)
C07D 487/04 (2006.01)

(52) U.S. Cl.
CPC .......... *C07D 487/04* (2013.01); *A61K 31/407* (2013.01)

(58) Field of Classification Search
CPC ..................... A61K 31/395; C07D 487/04
USPC .......................................... 514/183; 540/476
See application file for complete search history.

(56) References Cited

U.S. PATENT DOCUMENTS

2010/0273812 A1   10/2010   Wang et al.

FOREIGN PATENT DOCUMENTS

| CN | 111606970 A | 9/2020 |
|---|---|---|
| CN | 114727984 A | 7/2022 |
| WO | 2008128171 A2 | 10/2008 |
| WO | 2021148396 A1 | 7/2021 |

OTHER PUBLICATIONS

International Search Report in PCT/CN2023/108830 mailed on Sep. 20, 2023, 7 pages.
Written Opinion in PCT/CN2023/108830 mailed on Sep. 20, 2023, 5 pages.
Cai, Qian et al., A Potent and Orally Active Antagonist (SM-406/AT-406) of Multiple Inhibitor of Apoptosis Proteins (IAPs) in Clinical Development for Cancer Treatment, Journal of Medicinal Chemistry, 54: 2714-2726, 2011.

*Primary Examiner* — Douglas M Willis
(74) *Attorney, Agent, or Firm* — METIS IP LLC

(57) ABSTRACT

The present invention provides novel crystalline forms of Xevinapant and preparation methods thereof, pharmaceutical compositions containing the crystalline forms, and uses of the crystalline forms for preparing IAPs drugs and drugs for treating LA SCCHN.

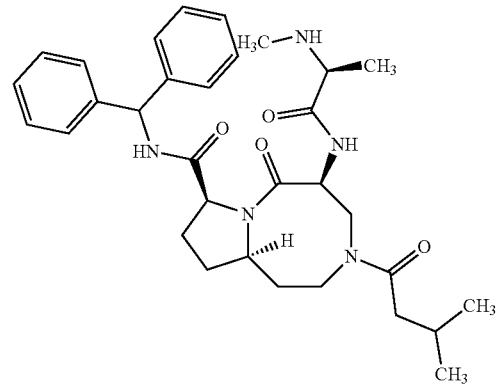

Compound I

10 Claims, 29 Drawing Sheets

CRYSTAL FORM OF XEVINAPANT FOR TREATING LA SCCHN

CROSS-REFERENCE TO RELATED APPLICATIONS

This application is a continuation of International Patent Application No. PCT/CN2023/108830, filed on Jul. 24, 2023, which claims priority to Chinese Patent Application No. 202210906912. X and No. 202211375174.7, filed on Jul. 29, 2022 and Nov. 4, 2022, respectively, the entire contents of which are incorporated herein by reference.

TECHNICAL FIELD

The present disclosure relates to the field of chemical crystallography, and in particular, to crystalline forms of Xevinapant, preparation method and use thereof.

BACKGROUND

Xevinapant is the first inhibitor of IAPs (Inhibitor of Apoptosis Proteins) to receive FDA breakthrough therapy designation. Combination with current nursing standards, Xevinapant is used to treating advanced squamous cell carcinoma of the head and neck (LA SCCHN) patients, and is developed by Debiopharma and Merck KGaA. The IAPs increase tumor cell sensitivity to chemoradiotherapy (CRT) by enhancing apoptosis and improving anti-tumor immune response. Xevinapant demonstrated efficacy in treating patients with LA SCCHN in a phase 2 clinical trial. Compared to CRT alone, combination with Xevinapant provided highly significant and sustainable clinical benefit. In addition to combination with the CRT, the Xevinapant is also being investigated in combination with chemotherapy as well as checkpoint inhibitors.

The chemical name of Xevinapant is (5S,8S,10aR)—N-benzhydryl-5-((S)-2-(methylamino)propanamido)-3-(3-methylbutanoyl)-6-oxodecahydropyrrolo[1,2-a][1,5]diazocine-8-carboxamide (hereinafter referred to as Compound I), and the structure is shown as the follows:

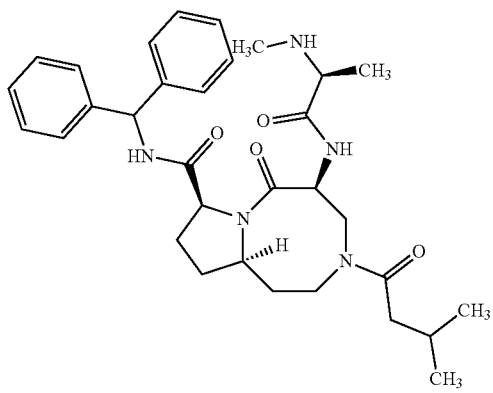

Compound I

As is well known in this field, drug polymorphism is a common phenomenon in the development of small molecule drugs and an important factor affecting drug quality. A crystalline form is a solid material whose constituents are arranged in a highly ordered microscopic structure, forming a crystal lattice that extends in all directions. Polymorphism refers to the phenomenon that a compound exists in more than one crystalline form. Compounds may exist in one or more crystalline forms, but their existence and characteristics cannot be predicted with any certainty. Different crystalline forms of drug substances have different physicochemical properties, including chemical stability, thermal stability, solubility, hygroscopicity and/or particle size, which may affect drug's in vivo dissolution and absorption and will further affect drug's clinical efficacy to some extent. In addition, drug substance with different crystal forms have different manufacturability, including yield, purification properties, filtration properties, drying properties, and grinding properties. The stability relative to pressure during tablet pressing may have an impact on the processing of drug substance during production. Therefore, polymorphism is an important part of drug research and drug quality control.

Example 16 of prior art WO2008128171A2 (referred to as prior art P1) disclosed the structure of Compound I hydrochloride, 1H NMR (MeOH-d4, 300 M Hz) data, and 13C NMR (MeOH-d4, 300 M Hz) thereof, but didn't disclose the preparation method of Compound I, and the polymorph of Compound I. Prior art literature "A Potent and Orally Active Antagonist (SM-406/AT-406) of Multiple Inhibitor of Apoptosis Proteins (IAPs) in Clinical Development for Cancer Treatment" (J. Med. Chem. 2011, 54, 8, 2714-2726, referred to as prior art P2), only disclosed the crude product of Compound I hydrochloride and the preparation method of Compound I trifluoroacetate. The specific method is as follows: the solution was stirred at room temperature overnight and then concentrated to give crude product which was purified by HPLC to give pure compound 2 (salt with TFA, 48 mg, 74% over three steps).

The present disclosure repeated the preparation method in prior art P2 and characterized the obtained products. The crude product is amorphous of Compound I hydrochloride (referred to as prior art Solid A). The compound 2 is amorphous of Compound I trifluoroacetate (referred to as prior art Solid B). The present disclosure has found that prior art Solid A and Solid B show poor stability. The purity of prior art Solid A and prior art Solid B decreased when stored under the condition of 25° C./60% RH with open package for one month. They transform into a transparent solid or a transparent gel after the DVS test at 0% RH-95% RH and being stored under the condition of 60° C./75% RH with open package for one week.

In order to overcome the disadvantages of prior arts, a novel crystalline form meeting the medicinal standard is still needed for the development of drugs containing the Compound I.

SUMMARY

One aspect of the present disclosure provides a crystalline form of Compound I,

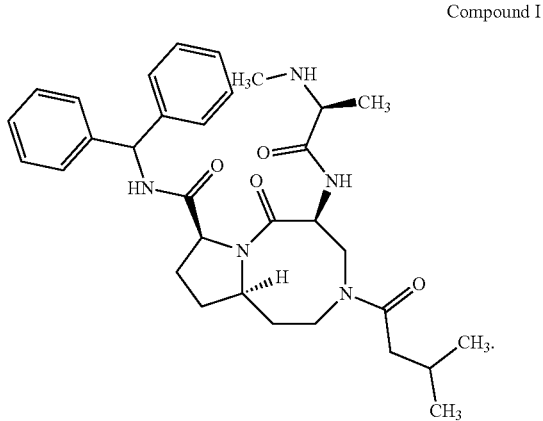

Compound I

In some embodiments, an X-ray powder diffraction pattern of the crystalline form includes one or two or three characteristic peaks at 2θ values of 12.5°±0.2°, 18.0°±0.2° and 10.2°±0.2° using Cu-Kα radiation.

In some embodiments, the X-ray powder diffraction pattern includes one or two or three characteristic peaks at 2θ values of 15.3°±0.2°, 9.3°±0.2° and 25.2°±0.2° using Cu-Kα radiation.

In some embodiments, the X-ray powder diffraction pattern is substantially as shown in FIG. 1 or FIG. 4 using Cu-Kα radiation.

In some embodiments, an X-ray powder diffraction pattern of the crystalline form includes one or two or three characteristic peaks at 2θ values of 12.8°±0.2°, 10.6°±0.2° and 14.7°±0.2° using Cu-Kα radiation.

In some embodiments, the X-ray powder diffraction pattern includes one or two or three characteristic peaks at 2θ values of 17.2°±0.2°, 18.3°±0.2° and 17.9°±0.2° using Cu-Kα radiation.

In some embodiments, the X-ray powder diffraction pattern includes one or two or three characteristic peaks at 2θ values of 16.2°±0.2° and 9.9°±0.2° using Cu-Kα radiation.

In some embodiments, the X-ray powder diffraction pattern is substantially as shown in FIG. 5 or FIG. 6 or FIG. 7 using Cu-Kα radiation.

One of the embodiments of the present disclosure provides a pharmaceutical composition, wherein the pharmaceutical composition includes a therapeutically effective amount of the crystalline form of Compound I, and pharmaceutically acceptable excipients.

One of the embodiments of the present disclosure provides a method of treating LA SCCHN, including administering to a subject in need thereof a therapeutically effective amount of the crystalline form of Compound I.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, and wherein.

DETAILED DESCRIPTION

The present disclosure is further illustrated by the following examples which describe the preparation and use of the crystal form of the present disclosure in detail. It is obvious to those skilled in the art that changes in the materials and methods may be accomplished without departing from the scope of the present disclosure.

The present disclosure is to provide novel crystalline forms of Compound I, preparation method, pharmaceutical compositions including the crystalline forms and use thereof.

According to the objective of the present disclosure, crystalline form CSI of the Compound I is provided by the present disclosure (hereinafter referred to as Form CSI).

In some embodiments, an X-ray powder diffraction pattern of the Form CSI includes one or two or three characteristic peaks at 2θ values of 12.5°±0.2°, 18.0°±0.2° and 10.2°±0.2° using Cu-Kα radiation. Preferably, the X-ray powder diffraction pattern of the Form CSI includes characteristic peaks at 2θ values of 12.5°±0.2°, 18.0°±0.2° and 10.2°±0.2° using Cu-Kα radiation.

In some embodiments, the X-ray powder diffraction pattern of the Form CSI includes one or two or three characteristic peaks at 2θ values of 15.3°±0.2°, 9.3°±0.2° and 25.2°±0.2° using Cu-Kα radiation. Preferably, the X-ray powder diffraction pattern of the Form CSI includes characteristic peaks at 2θ values of 15.3°±0.2°, 9.3°±0.2° and 25.2°±0.2° using Cu-Kα radiation.

In some embodiments, the X-ray powder diffraction pattern of the Form CSI includes one or two or three or four or five or six or seven or eight or nine or ten or eleven or twelve characteristic peaks at 2θ values of 12.5°±0.2°, 18.0°±0.2°, 10.2°±0.2°, 15.3°±0.2°, 9.3°±0.2°, 25.2°±0.2°, 6.2°±0.2°, 16.1°±0.2°, 17.5°±0.2°, 18.8°±0.2°, 20.8°±0.2° and 23.7°±0.2° using Cu-Kα radiation.

Figure 1:
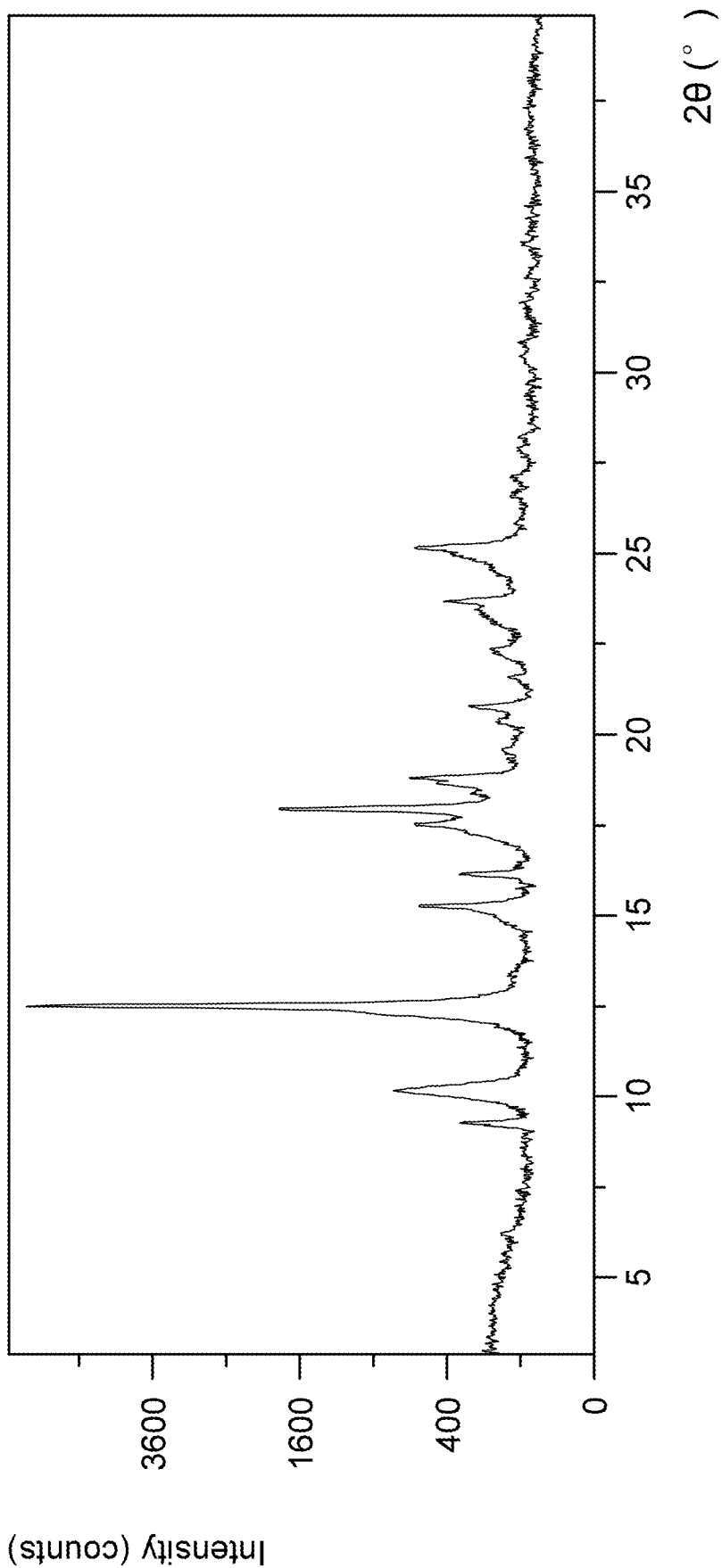
FIG. 1 is an XRPD pattern of Form CSI according to some embodiments of the present disclosure.
Figure 4:
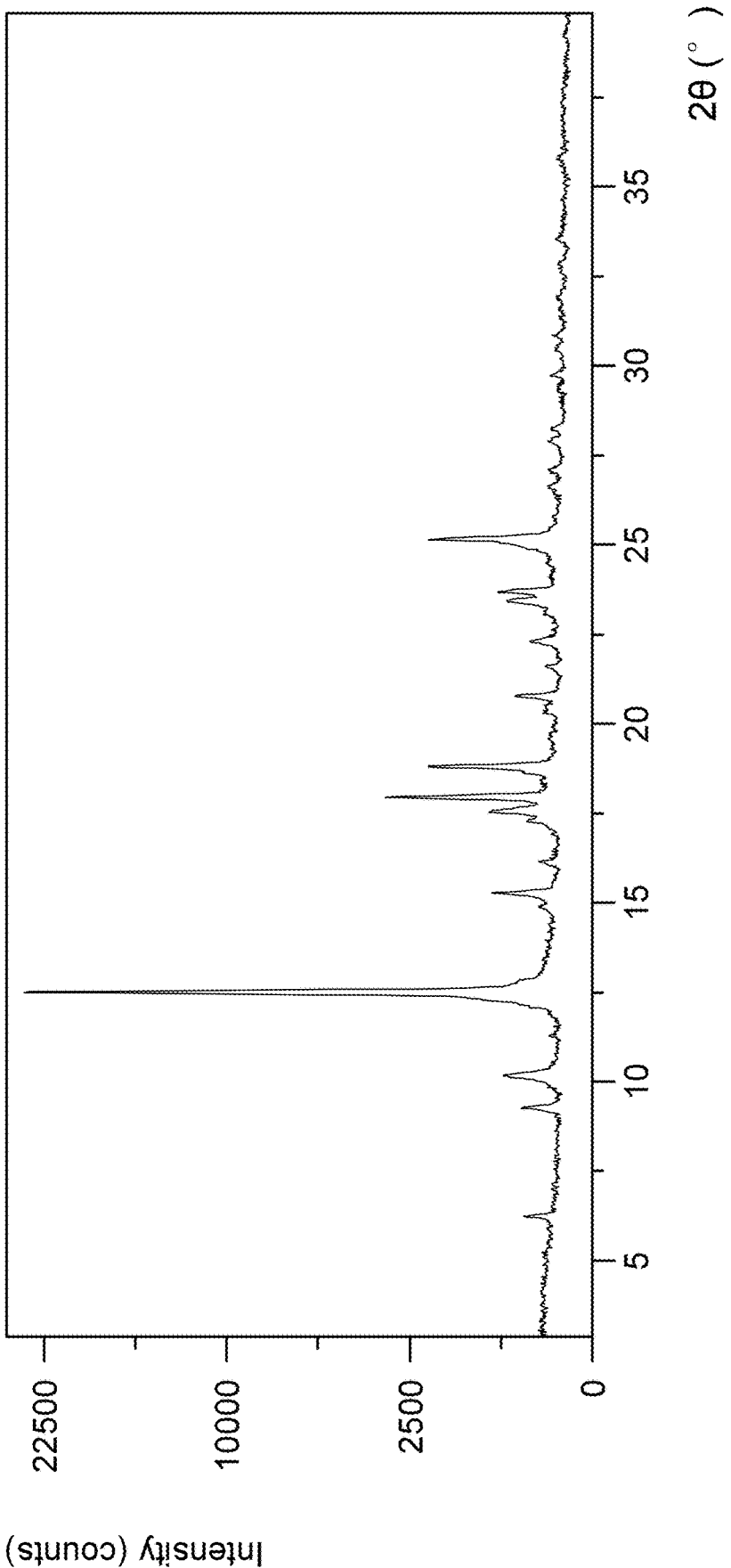
FIG. 4 is an XRPD pattern of the Form CSI according to some embodiments of the present disclosure.

In some embodiments, an XRPD pattern of the Form CSI is substantially as shown in FIG. 1 or FIG. 4.

Figure 2:
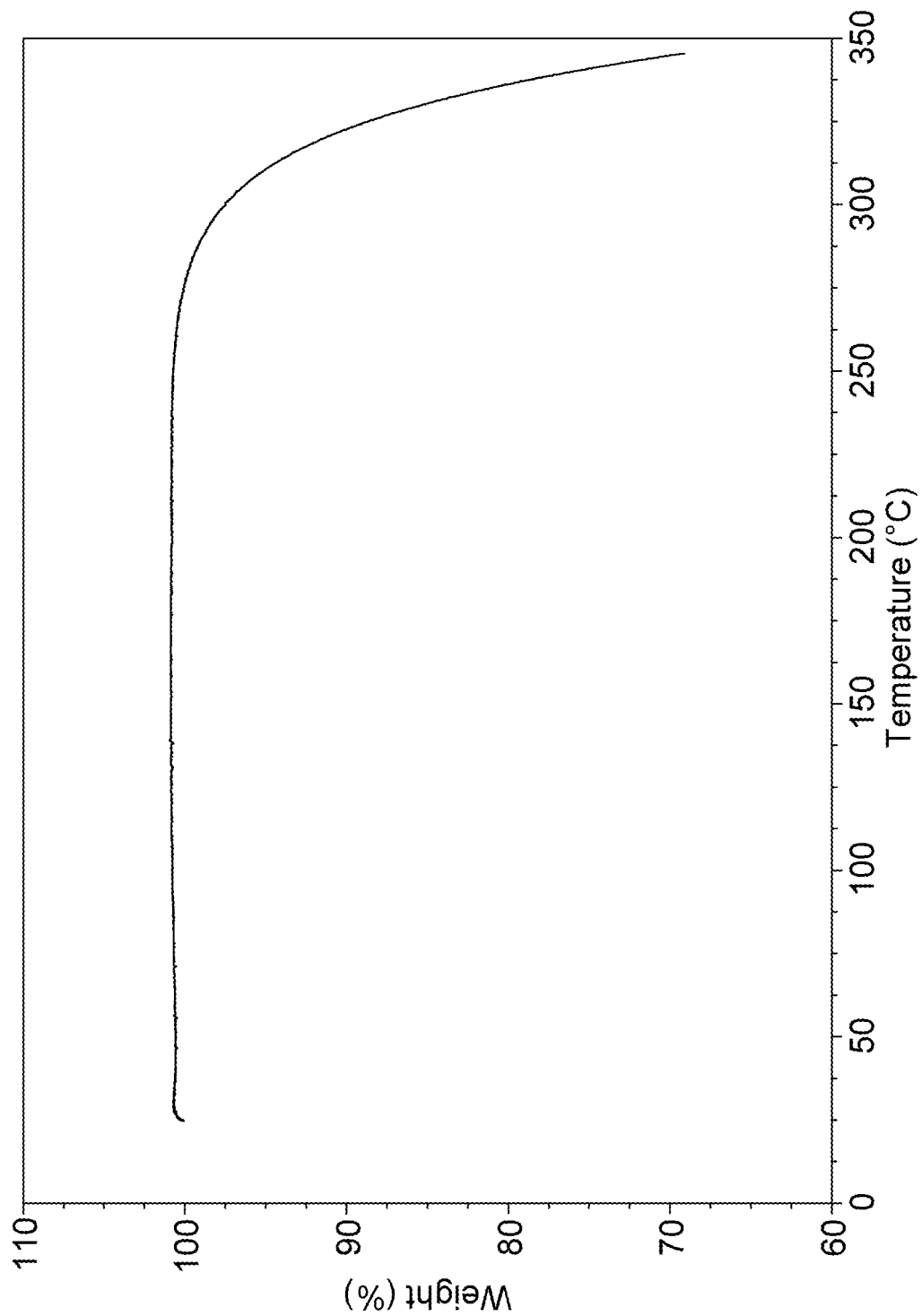
FIG. 2 is a TGA curve of the Form CSI according to some embodiments of the present disclosure.

In some embodiments, a TGA curve of the Form CSI is substantially as shown in FIG. 2, which shows almost no weight loss when heated from room temperature to 190° C.

Figure 3:
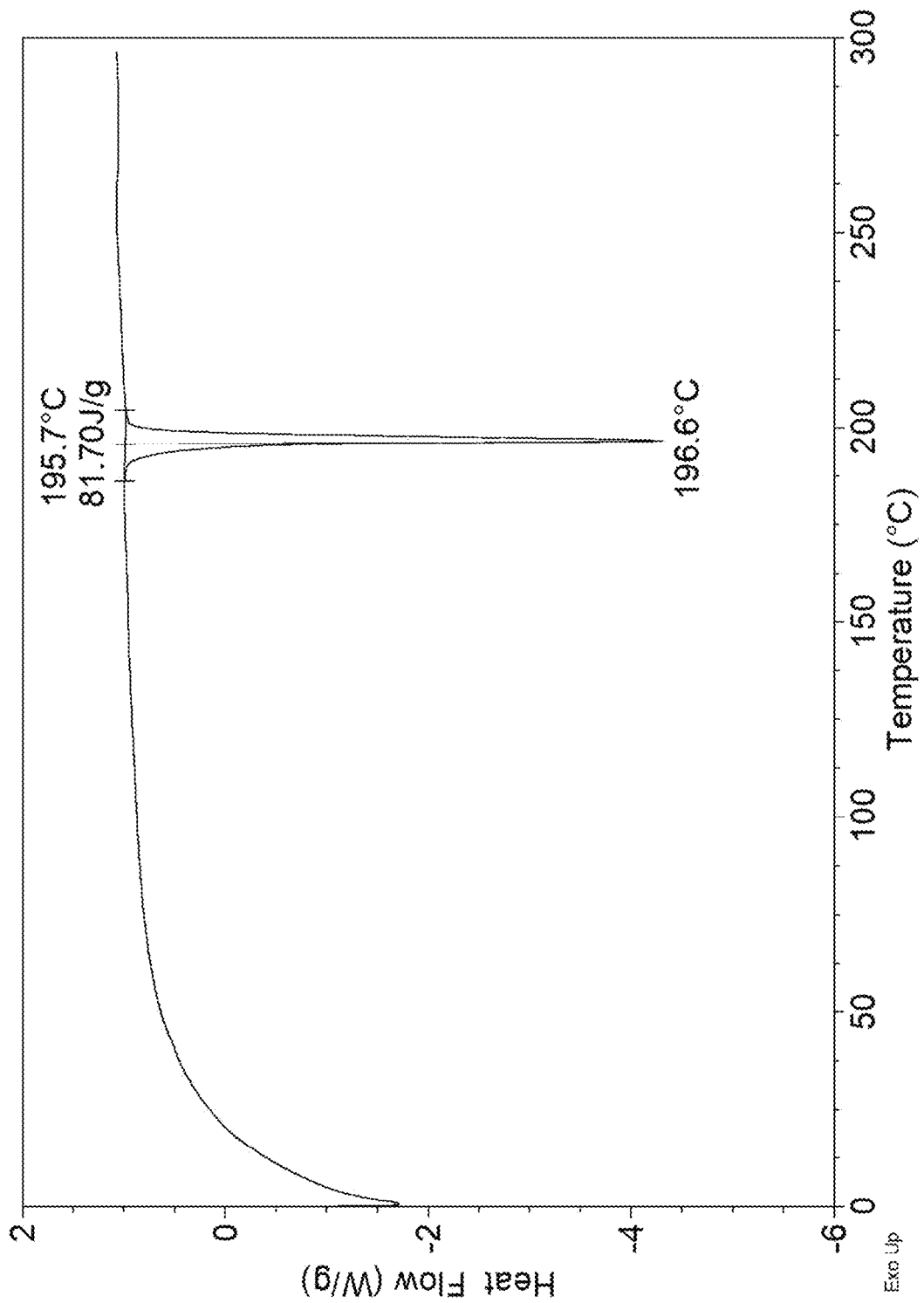
FIG. 3 is a DSC curve of the Form CSI according to some embodiments of the present disclosure.

In some embodiments, a DSC curve of the Form CSI is substantially as shown in FIG. 3, which shows an endothermic peak at about 196° C.

According to the objective of the present disclosure, a process for preparing the Form CSI is also provided. The process includes:

Method 1: adding the Compound I into methyl tert-butyl ether, stirring at room temperature for two days to obtain the Form CSI; or Method 2: dissolving the Compound I into tetrahydrofuran or ethyl acetate, evaporating at room temperature to obtain the Form CSI.

According to the objective of the present disclosure, crystalline form CSII of the Compound I is provided by the present disclosure (hereinafter referred to as Form CSII).

In some embodiments, an X-ray powder diffraction pattern of the Form CSII includes one or two or three characteristic peaks at 2θ values of 12.8°±0.2°, 10.6°±0.2° and 14.7°±0.2° using Cu-Kα radiation. Preferably, the X-ray powder diffraction pattern of the Form CSII includes characteristic peaks at 2θ values of 12.8°±0.2°, 10.6°±0.2° and 14.7°±0.2° using Cu-Kα radiation.

In some embodiments, the X-ray powder diffraction pattern of the Form CSII includes one or two or three characteristic peaks at 2θ values of 17.2°±0.2°, 18.3°±0.2° and 17.9°±0.2° using Cu-Kα radiation. Preferably, the X-ray powder diffraction pattern of the Form CSII includes characteristic peaks at 2θ values of 17.2°±0.2°, 18.3°±0.2° and 17.9°±0.2° using Cu-Kα radiation.

In some embodiments, the X-ray powder diffraction pattern of the Form CSII includes one or two characteristic peaks at 2θ values of 16.2°±0.2° and 9.9°±0.2° using Cu-Kα radiation. Preferably, the X-ray powder diffraction pattern of the Form CSII includes characteristic peaks at 2θ values of 16.2°±0.2° and 9.9°±0.2° using Cu-Kα radiation.

In some embodiments, the X-ray powder diffraction pattern of the Form CSII includes one or two or three or four or five or six or seven or eight or nine or ten or eleven or twelve or thirteen or fourteen or fifteen characteristic peaks at 2θ values of 9.9°±0.2°, 10.6°±0.2°, 12.8°±0.2°, 14.7°±0.2°, 15.4°±0.2°, 16.2°±0.2°, 17.2°±0.2°, 17.9°±0.2°, 18.3°±0.2°, 19.3°±0.2°, 20.4°±0.2°, 21.2°±0.2°, 23.2°±0.2°, 24.4°±0.2° and 25.8°±0.2° using Cu-Kα radiation.

Figure 5:
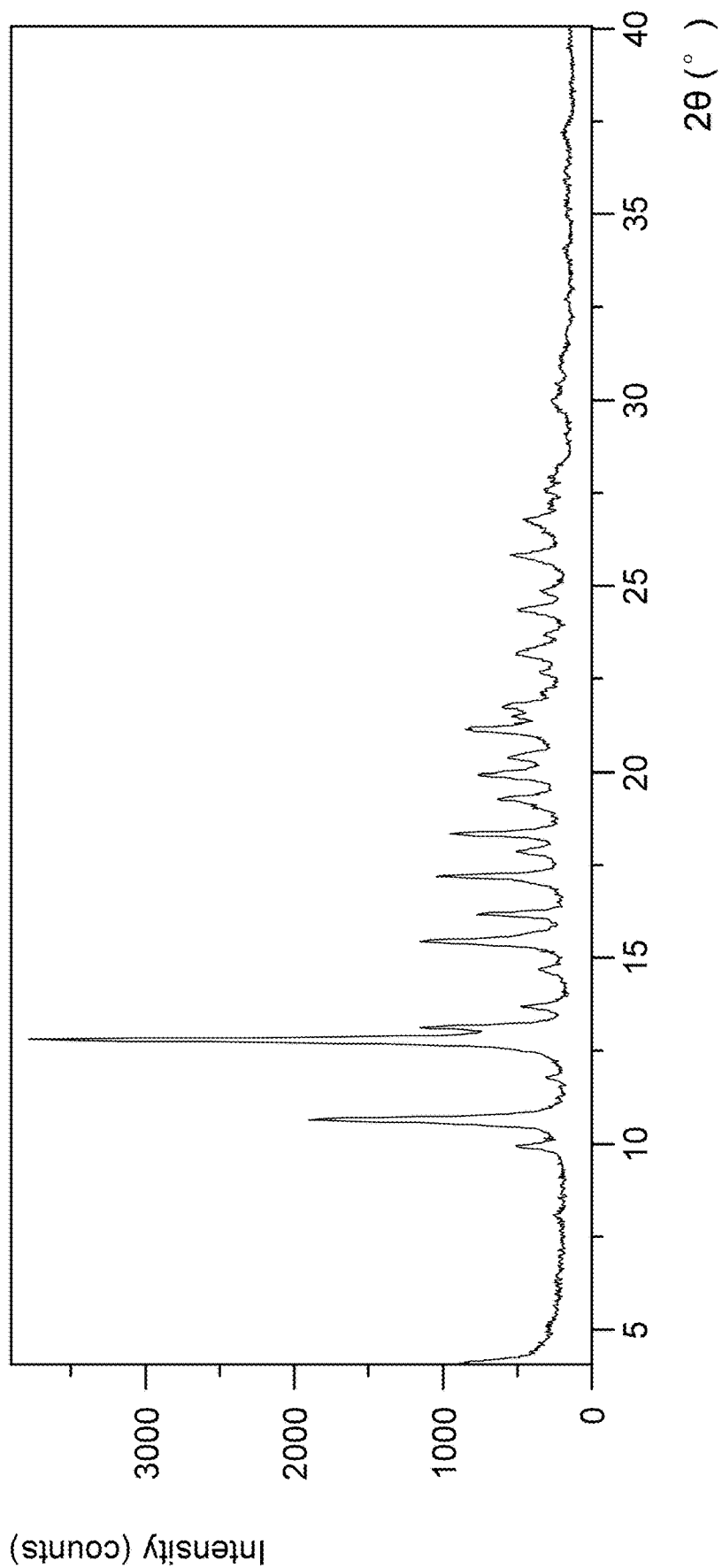
FIG. 5 is an XRPD pattern of Form CSII according to some embodiments of the present disclosure.
Figure 6:
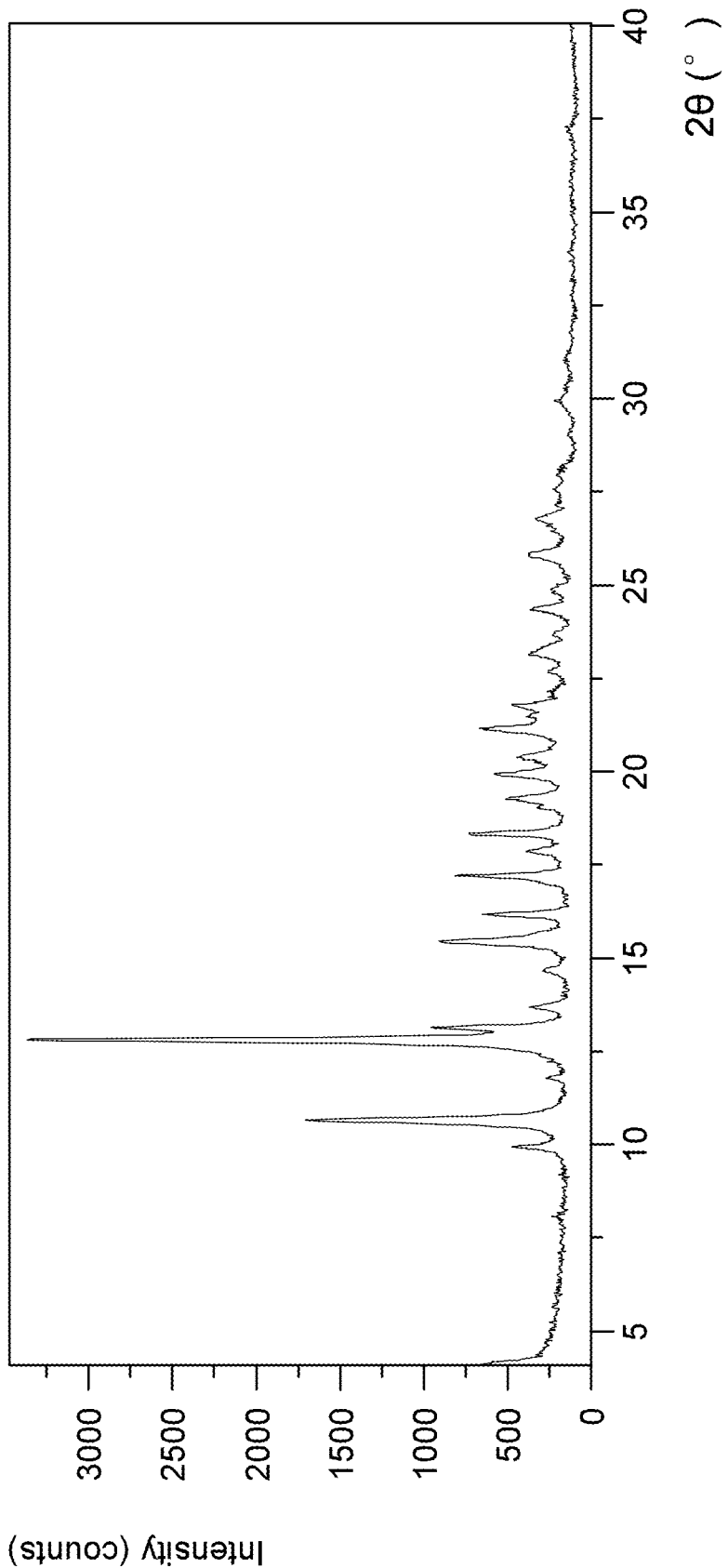
FIG. 6 is an XRPD pattern of the Form CSII according to some embodiments of the present disclosure.
Figure 7:
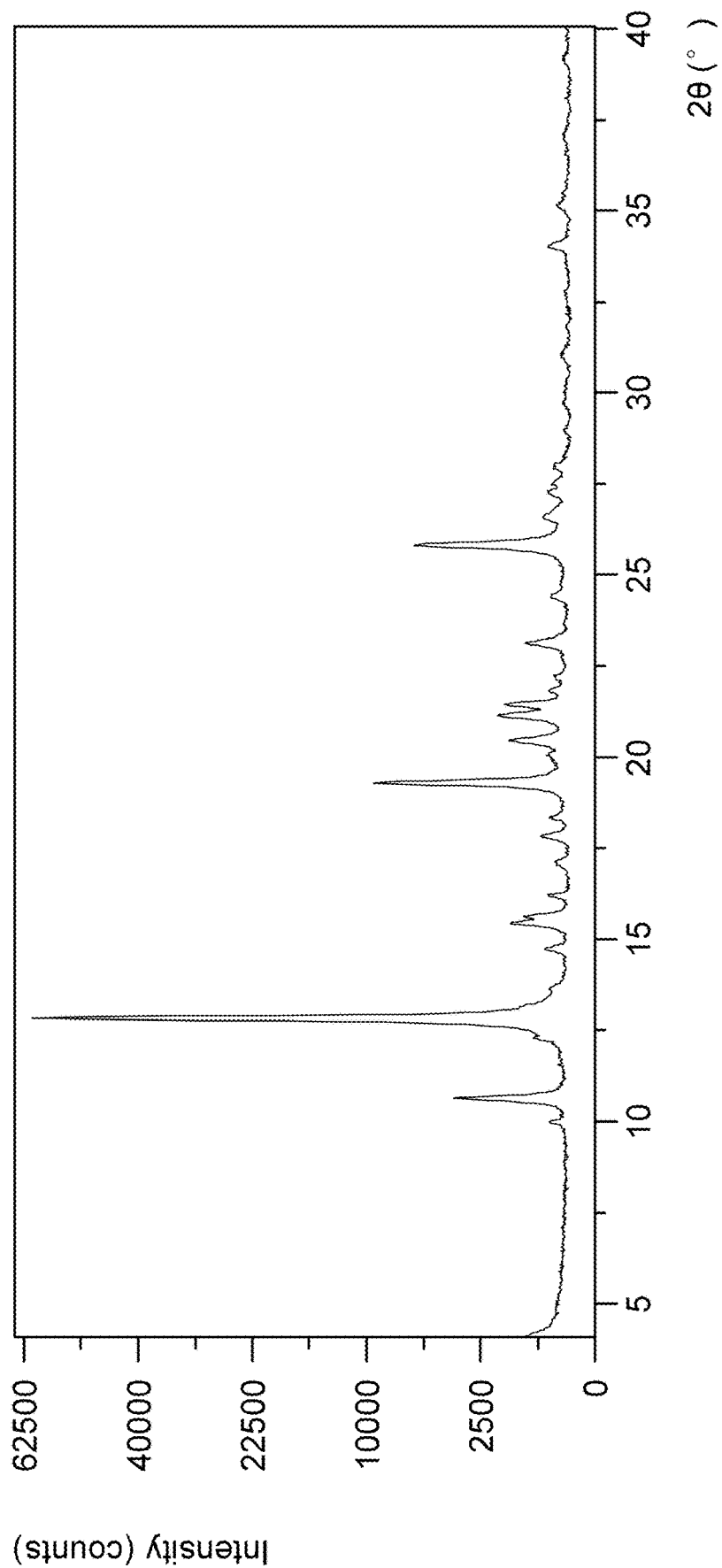
FIG. 7 is an XRPD pattern of the Form CSII according to some embodiments of the present disclosure.

In some embodiments, the X-ray powder diffraction pattern of the Form CSII is substantially as shown in FIG. 5, FIG. 6, or FIG. 7.

Figure 8:
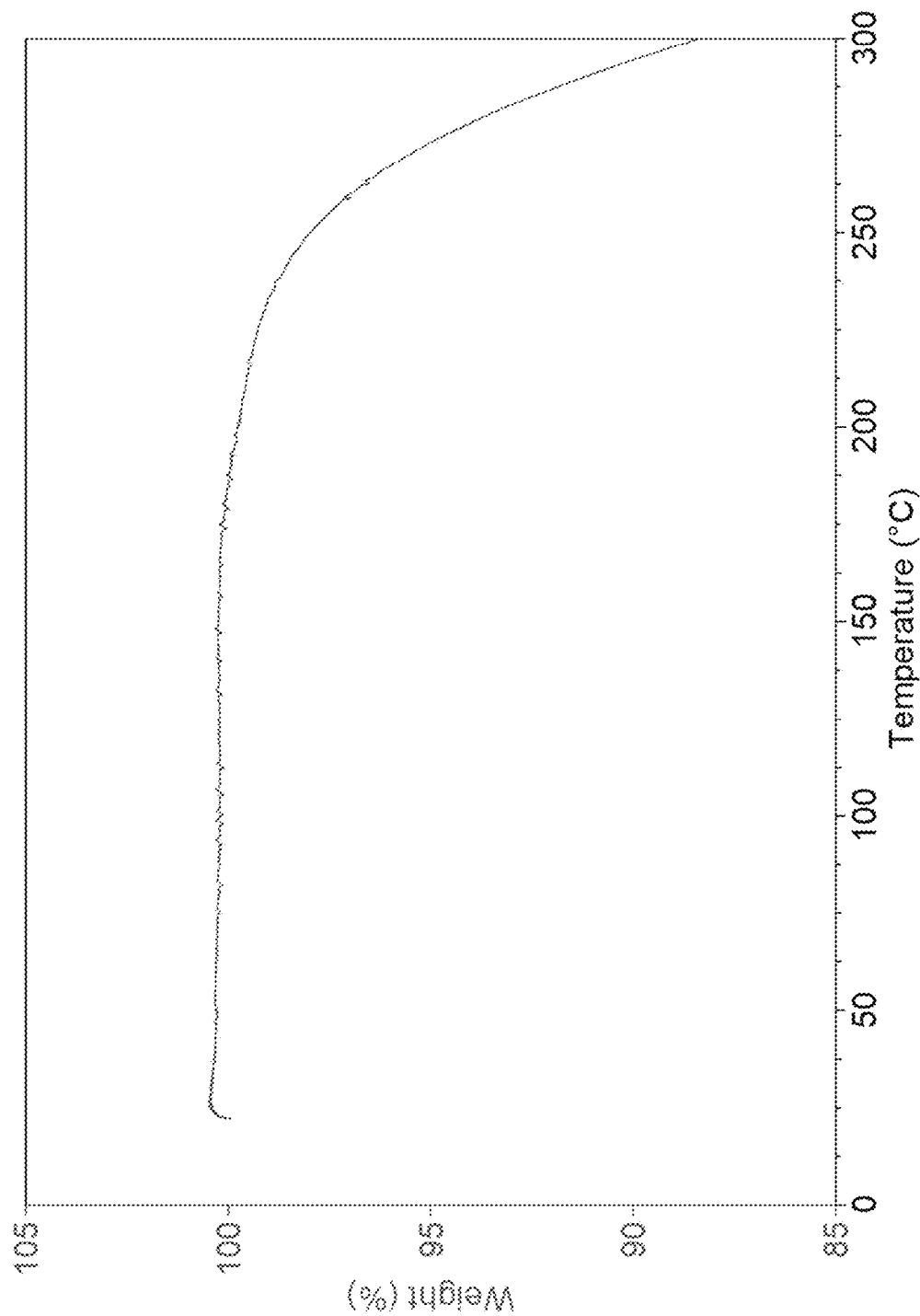
FIG. 8 is a TGA curve of the Form CSII according to some embodiments of the present disclosure.

In some embodiments, a TGA curve of the Form CSII is substantially as shown in FIG. 8, which shows almost no weight loss when heated from room temperature to 175° C.

According to the objective of the present disclosure, a process for preparing the Form CSII is also provided. The process includes:

Method 1: dissolving the Compound I into toluene by heating, cooling at −20° C. to obtain the Form CSII.

Method 2: exposing the Compound I amorphous to 60° C./75% RH for one week to obtain the Form CSII.

According to the objective of the present disclosure, the Form CSI and/or the Form CSII may be used for preparing other crystalline forms or salts or co-crystals of the Compound I.

According to the objective of the present disclosure, a pharmaceutical composition is provided, the pharmaceutical composition includes a therapeutically effective amount of the Form CSI and/or the Form CSII and pharmaceutically acceptable excipients.

In some embodiments, the Form CSI and/or the Form CSII may be used for preparing IAPs drugs.

In some embodiments, the Form CSI and/or the Form CSII may be used for preparing drugs treating LA SCCHN.

The technical problems solved by the present disclosure are poor physicochemical stability and high solvent residue in prior art solids. The present disclosure provides crystalline forms of the Compound I, which have better physicochemical stability, higher purity, and no solvent residue compared to prior art solids, while also having minimal hygroscopicity and weight gain. These advantages solve the problems existing in prior arts.

The Form CSI of the present disclosure has following advantages:

(1) The Form CSI drug substance of the present disclosure has good physicochemical stability. The purity of the prior art Solid A and the prior art Solid B decreased when stored under the condition of 25° C./60% RH with open package for one month. In addition, the prior art Solid A and the prior art Solid B are prone to deliquescence. They transform into a transparent gel after being stored under the condition of 60° C./75% RH with open package for one week, and transformed into a transparent solid after the DVS test at 0% RH-95% RH. Crystalline state of the Form CSI drug substance doesn't change for at least 6 months when stored under the condition of 25° C./60% RH with open package. The crystalline state of Form CSI drug substance doesn't change for at least 3 months when stored under the condition of 60° C./75% RH with open package. The chemical purity remains substantially unchanged during storage. After the DVS test at 0% RH-95% RH, there was no significant change in sample properties and no change in crystalline state of the Form CSI drug substance.

These results show that the Form CSI drug substance has better stability under long-term, stress and high humidity conditions compared with prior arts. Drug substance would go through high temperature and high humidity conditions caused by different season, regional climate and environment during storage, transportation, and manufacturing processes. Therefore, good stability under long-term, stress and high humidity conditions is of great importance to the drug development. The Form CSI drug substance has better stability under long-term, stress and high humidity conditions, which is beneficial to avoid the impact on drug quality due to crystal transformation or decrease in purity during drug storage.

(2) Compared with prior arts, the Form CSI of the present disclosure has higher purity. Prior art P2 disclosed that the purity of the Compound I trifluoroacetate amorphous after purification is over 95%. The present disclosure repeated the prior arts and obtained the purity of the prior art Solid A, the prior art Solid B and the Form CSI through HPLC test. The results show that the purity of the prior art Solid A and the prior art Solid B is 98.77% and 98.87%, respectively. The purity of the Form CSI is 99.50%, which is higher than that of prior art solids.

(3) The Form CSI of the present disclosure has minimal hygroscopicity. The weight gain of the Form CSI from 0% to 80% RH is 0.46%. High hygroscopicity tends to cause chemical degradation and polymorph transformation, which directly affects the physicochemical stability of the drug substance. Meanwhile, drugs with high hygroscopicity will have higher requirements for production.

(4) The Form CSI has good physical stability under mechanical force. The crystalline state of the Form CSI doesn't change after grinding. Grinding and pulverization are often required in drug manufacturing process. Good physical stability of the drug substance may reduce the risk of crystallinity decrease and crystal transformation during drug production process. The Form CSI has good physical stability under different pressures, which is beneficial to keep crystal unchanged during tableting process.

(5) The From CSI drug product of the present disclosure has good physical stability. After the Form CSI is mixed with the excipients to form a drug product and stored under the condition of 40° C./75% RH, crystalline state of the Form CSI drug product doesn't change for at least one month. These results show that the From CSI product of the present disclosure has good stability under accelerated condition, which is beneficial to drug storage.

The present disclosure surprisingly obtained crystalline forms of the Compound I, which have advantages in at least one aspect of solubility, hygroscopicity, purification ability, stability, adhesiveness, compressibility, flowability, in vitro and in vivo dissolution, and bioavailability, etc. In particular, the crystalline forms of the Compound I of the present disclosure have advantages such as good stability, low hygroscopicity, no solvent residue, high purity, which solve the problems existing in prior arts and are of great significance for the development of drugs containing the Compound I.

EXAMPLE

The abbreviations used in the present disclosure are explained as follows:
XRPD: X-ray Powder Diffraction
GC: Gas Chromatography
TGA: Thermo Gravimetric Analysis
DSC: Differential Scanning calorimetry
DVS: Dynamic Vapor Sorption
HPLC: High Performance Liquid Chromatography
RH: Relative humidity Instruments and methods used for data collection:
X-ray powder diffraction patterns in the present disclosure were acquired by a Bruker X-ray powder diffractometer. The parameters of the X-ray powder diffraction method of the present disclosure are as follows:
X-Ray source: Cu, Kα
Kα1 (Å): 1.54060, Kα2 (Å): 1.54439
Kα2/Kα1 intensity ratio: 0.50

Thermo gravimetric analysis (TGA) data in the present disclosure were acquired by a TA Q500. The parameters of the TGA method of the present disclosure are as follows:
Heating rate: 10° C./min
Purge gas: $N_2$ Differential scanning calorimetry (DSC) data in the present disclosure were acquired by a TA Q2000. The parameters of the DSC method of the present disclosure are as follows:
Heating rate: 10° C./min
Purge gas: $N_2$
Dynamic Vapor Sorption (DVS) was measured via an SMS (Surface Measurement Systems Ltd.) intrinsic DVS instrument. The instrument control software is DVS-Intrinsic control software. Typical Parameters for DVS test are as follows:
Temperature: 25° C.
Gas and flow rate: $N_2$, 200 mL/min
dm/dt: 0.002%/min
RH range: 0% RH-95% RH
The parameters of related substance detection in the present disclosure are shown in Table 1.

TABLE 1

| HPLC | Agilent 1260 |
|---|---|
| Column | Waters XBridge C18, 4.6 × 150 mm, 3.5 μm |
| Ghost-Buster column | Welch Ghost-Buster, 4.6 × 50 mm |
| Mobile phase | A: 10 mM $KH_2PO_4$ (aq) (pH 8.0, NaOH) |
| | B: Acetonitrile: Methanol = 700:300 (v/v) |

| Gradient | Time (min) | % A |
|---|---|---|
| | 0.0 | 45 |
| | 2.0 | 45 |
| | 30.0 | 80 |
| | 32.0 | 80 |
| | 33.0 | 45 |
| | 40.0 | 45 |
| Flow rate | 1.0 mL/min | |
| Injection volume | 10 μL | |
| Detector wavelength | 210 nm | |
| Column temperature | 40° C. | |
| Diluent | Methanol | |

The parameters of GC detection for residual solvents in the present disclosure are shown in Table 2.

TABLE 2

| Instrument | Agilent 7890B GC system |
|---|---|
| Column | DB-624UI, 30 m × 0.32 mm, 1.8 μm |
| Carrier gas | $N_2$ |
| Temperature programming | Maintain 50° C. for 3 minutes, and then heat up to 83° C. at 3° C./min. Maintain 80° C. for 1 minute, and then heat up to 220° C. at 40° C./min. Maintain 220° C. for 5 minutes |
| Run time | 23.425 min |
| Injector temperature | 230° C. |
| Split ratio | 20:1 |
| Injection volume | 1 mL |
| Flow rate | 1.0 mL/min |
| Detector | FID |
| Detector temperature | 250° C. |
| Hydrogen flow rate | 30 mL/min |
| Air flow rate | 350 mL/min |
| Make-up gas flow rate | 26 mL/min |
| Furnace temperature | 100° C. |
| Quantitative loop temperature | 110° C. |
| Transmission line temperature | 120° C. |
| Balance time | 20 min |
| GC cycle time | 30 min |

In the present disclosure, the "stirring" is accomplished by using a conventional method in the field such as magnetic stirring or mechanical stirring and the stirring speed is 50 to 1800 r/min. Preferably the magnetic stirring speed is 300 to 900 r/min and mechanical stirring speed is 100 to 300 r/min.

The "evaporating" is accomplished by using a conventional method in the field such as slow evaporation or rapid evaporation. Slow evaporation is accomplished in a container covered by a sealing film with pinholes. Rapid evaporation is accomplished in an open container.

The "room temperature" is not a specific temperature, but a temperature range of 10-30° C.

The "characteristic peak" refers to a representative diffraction peak used to distinguish crystals. The 2θ value of diffraction peak usually may have a deviation of ±0.2° using Cu-Kα radiation.

In the present disclosure, amorphous forms are non-crystalline materials which possess no long-range order. Typically, an amorphous form will exhibit a broad "halo" XRPD pattern.

In the present disclosure, "crystal" or "crystalline form" refers to the crystal or the crystalline form being identified by the X-ray diffraction pattern shown herein. The X-ray powder diffraction pattern depend on the instrument conditions, the sample preparation and the purity of samples. The relative intensity of the diffraction peaks in the X-ray diffraction pattern may also vary with the experimental conditions; therefore, the order of the diffraction peak intensities may not be regarded as the sole or decisive factor. In fact, the relative intensity of the diffraction peaks in the X-ray powder diffraction pattern is related to the preferred orientation of the crystals, and the diffraction peak intensities shown herein are illustrative and identical diffraction peak intensities are not required. Thus, a crystalline form of the present disclosure is not necessarily to have exactly the same X-ray diffraction pattern of the example shown herein. Any crystalline forms whose X-ray diffraction patterns have the same or similar characteristic peaks should be within the scope of the present disclosure. Comparing the patterns shown in the present disclosure with that of an unknown crystalline form in order to identify whether these two groups of patterns reflect the same or different crystalline forms.

In some embodiments, Form CSI and Form CSII of the present disclosure are pure and substantially free of any other crystalline forms. In the present disclosure, the term "substantially free" when used to describe a novel crystalline form, it means that the content of other crystalline forms in the novel crystalline form is less than 20% (w/w), specifically less than 10% (w/w), more specifically less than 5% (w/w) and furthermore specifically less than 1% (w/w).

In the present disclosure, the term "about" when referring to a measurable value such as weight, time, temperature, and the like, is meant to encompass variations of ±10%, ±5%, ±1%, ±0.5%, or even ±0.1% of the specified amount.

Unless otherwise specified, the following examples were conducted at room temperature.

According to the present disclosure, Compound I used as raw materials include, but are not limited to solid (crystalline and amorphous), oil, liquid or solution. Preferably, Compound I used as the raw material is a solid.

Raw materials of Compound I used in the following examples were prepared by prior arts, for example, the method disclosed in WO2008128171A2 combined with conventional salt breaking methods in this field.

Example 1: Preparation of Form CSI 9.3 mg of Compound I solid was placed in a vial, and then 0.5 mL of methyl tert-butyl ether was added. After stirring at room temperature for two days, the solid was separated by centrifugation, and then vacuum dried at room temperature for about four hours. Form CSI was obtained. An XRPD pattern is shown in FIG. 1, and an XRPD data are listed in Table 3.

A TGA curve of the Form CSI shows the Form CSI has almost no weight loss when heated from room temperature to 190° C., which is shown in FIG. 2.

A DSC curve of the Form CSI is shown in FIG. 3, which shows one endothermic peak at around 196° C. (onset temperature), corresponding to the melting point of the Form CSI.

TABLE 3

| 2θ (°) | d spacing (Å) | Relative intensity (%) |
| --- | --- | --- |
| 6.2 | 14.2 | 0.7 |
| 9.3 | 9.5 | 4.1 |
| 10.2 | 8.7 | 11.3 |
| 12.3 | 7.2 | 13.7 |
| 12.5 | 7.1 | 100.0 |
| 15.3 | 5.8 | 8.4 |
| 16.1 | 5.5 | 4.5 |
| 17.5 | 5.1 | 8.7 |
| 17.9 | 4.9 | 30.3 |
| 18.7 | 4.8 | 6.3 |
| 18.8 | 4.7 | 9.4 |
| 19.6 | 4.5 | 1.4 |
| 20.4 | 4.4 | 1.6 |
| 20.8 | 4.3 | 3.6 |
| 21.6 | 4.1 | 1.0 |
| 22.3 | 4.0 | 1.9 |
| 23.7 | 3.8 | 5.9 |
| 25.2 | 3.5 | 9.0 |
| 26.6 | 3.3 | 0.8 |
| 28.0 | 3.2 | 0.4 |
| 30.6 | 2.9 | 0.4 |
| 31.8 | 2.8 | 0.3 |
| 33.6 | 2.7 | 0.4 |

Example 2: Preparation of Form CSI 1.9 mg of Compound I solid was placed in a vial, and 0.2 mL of ethyl acetate was added to obtain a clear solution. The clear solution was evaporated at room temperature overnight to obtain Form CSI. An XRPD pattern of the Form CSI is shown in FIG. 4, and an XRPD data are listed in Table 4.

TABLE 4

| 2θ (°) | d spacing (Å) | Intensity (%) |
| --- | --- | --- |
| 6.2 | 14.2 | 0.9 |
| 9.3 | 9.5 | 1.1 |
| 10.2 | 8.7 | 2.1 |
| 11.3 | 7.8 | 0.1 |
| 12.5 | 7.1 | 100.0 |
| 15.3 | 5.8 | 2.8 |
| 16.1 | 5.5 | 0.6 |
| 17.3 | 5.1 | 1.0 |
| 17.5 | 5.1 | 2.8 |
| 18.0 | 4.9 | 12.7 |
| 18.8 | 4.7 | 8.0 |
| 19.6 | 4.5 | 0.3 |
| 20.4 | 4.4 | 0.4 |
| 20.8 | 4.3 | 1.5 |
| 21.6 | 4.1 | 0.4 |
| 22.3 | 4.0 | 0.9 |
| 23.4 | 3.8 | 1.9 |
| 23.7 | 3.8 | 2.4 |
| 25.2 | 3.5 | 7.7 |
| 26.6 | 3.3 | 0.3 |
| 27.1 | 3.3 | 0.3 |
| 27.9 | 3.2 | 0.3 |
| 28.2 | 3.2 | 0.2 |
| 29.4 | 3.0 | 0.1 |

TABLE 4-continued

| 2θ (°) | d spacing (Å) | Intensity (%) |
| --- | --- | --- |
| 29.7 | 3.0 | 0.3 |
| 30.5 | 2.9 | 0.2 |
| 30.9 | 2.9 | 0.2 |
| 31.9 | 2.8 | 0.1 |
| 32.8 | 2.7 | 0.1 |
| 33.6 | 2.7 | 0.2 |
| 35.8 | 2.5 | 0.1 |

Example 3: Preparation of Form CSII

Compound I solid was placed in a culture dish. After heating to 210° C., the solid was melted. Then, amorphous of Compound I was obtained after placing the culture dish into cold water. The amorphous of the Compound I was exposed under 60° C./75% RH environment for one week. Crystalline solid was obtained. The crystalline solid was confirmed as the Form CSII after test. An XRPD pattern is shown in FIG. 5.

Example 4: Preparation of Form CSII

Form CSII obtained from Example 3 was exposed under 60° C./75% RH environment for four weeks. No crystal change was observed, and the solid form is still the Form CSII. An XRPD pattern is shown in FIG. 6, and an XRPD data are listed in Table 5.

TABLE 5

| 2θ (°) | d spacing (Å) | Intensity (%) |
| --- | --- | --- |
| 9.9 | 8.9 | 9.8 |
| 10.6 | 8.3 | 48.0 |
| 12.8 | 6.9 | 100.0 |
| 13.1 | 6.7 | 24.6 |
| 13.7 | 6.5 | 6.8 |
| 14.7 | 6.0 | 4.4 |
| 15.4 | 5.7 | 23.4 |
| 16.2 | 5.5 | 15.4 |
| 17.2 | 5.2 | 20.8 |
| 17.9 | 5.0 | 7.8 |
| 18.3 | 4.8 | 18.5 |
| 19.0 | 4.7 | 5.4 |
| 19.3 | 4.6 | 11.4 |
| 19.9 | 4.5 | 13.0 |
| 20.4 | 4.4 | 9.5 |
| 21.2 | 4.2 | 15.4 |
| 21.8 | 4.1 | 10.6 |
| 22.7 | 3.9 | 4.1 |
| 23.2 | 3.8 | 7.8 |
| 24.4 | 3.7 | 6.9 |
| 25.8 | 3.5 | 8.0 |
| 26.8 | 3.3 | 6.7 |

Example 5: Preparation of Form CSII 99.0 mg of Compound I solid was added into a vial, and 4.0 mL of toluene was added thereafter. Clear solution was obtained after heating. The solution was filtrated. Solid was precipitated out after standing the filtrate at −20° C. for two days. The solid was separated by centrifugation, and then vacuum dried at room temperature for about 23 hours. Form CSII was obtained. An XRPD pattern is shown in FIG. 7.

Example 6: TGA Curve of Form CSII

A TGA curve of the Form CSII is shown in FIG. 8, which shows the Form CSII has almost no weight loss when heated from room temperature to 175° C.

Example 7: Preparation and Characterization of Prior Art Solids

Figure 9:
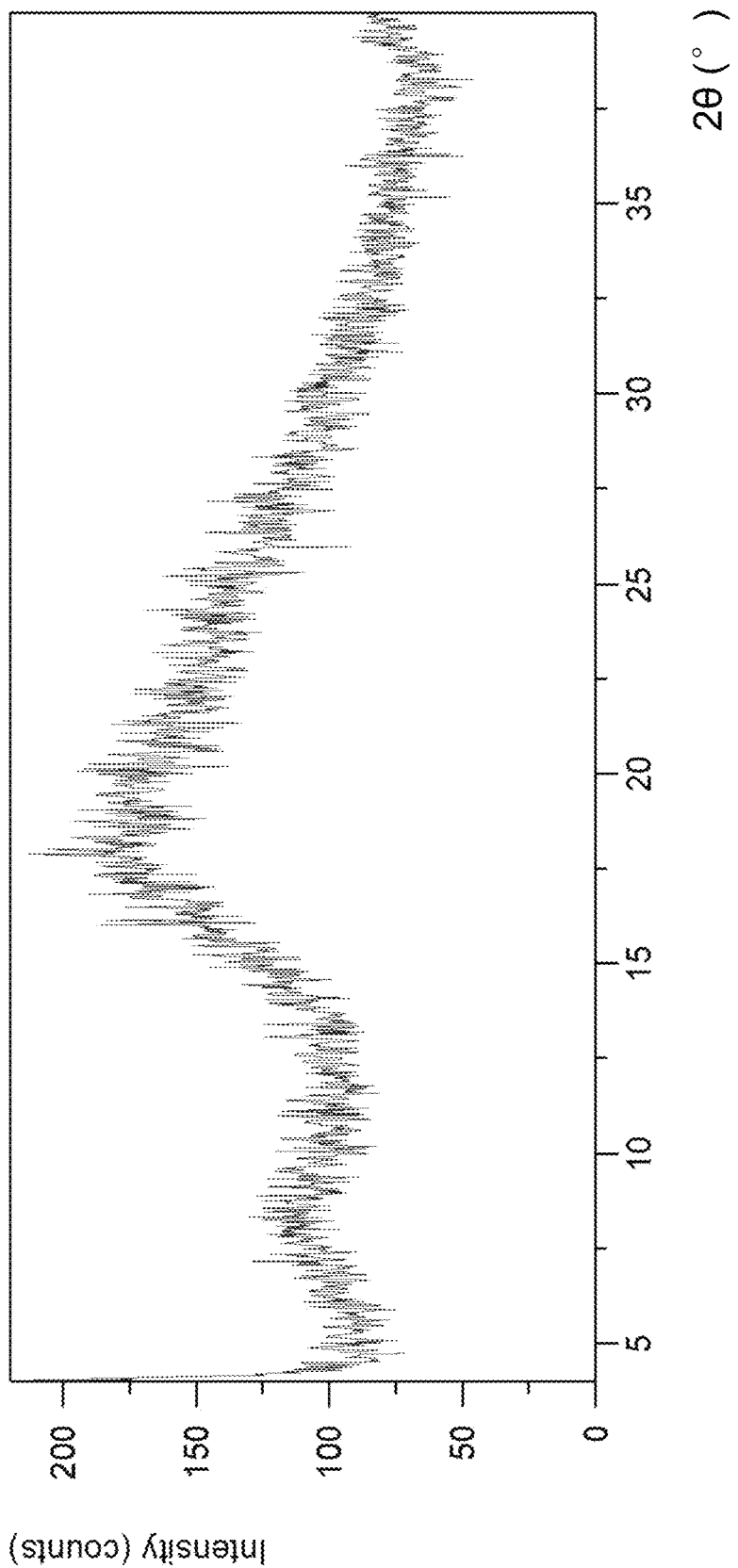
FIG. 9 is an XRPD pattern of prior art Solid A according to some embodiments of the present disclosure.

Prior art Solid A was obtained after repeating prior art P2, and an XRPD pattern is shown in FIG. 9.

Figure 10:
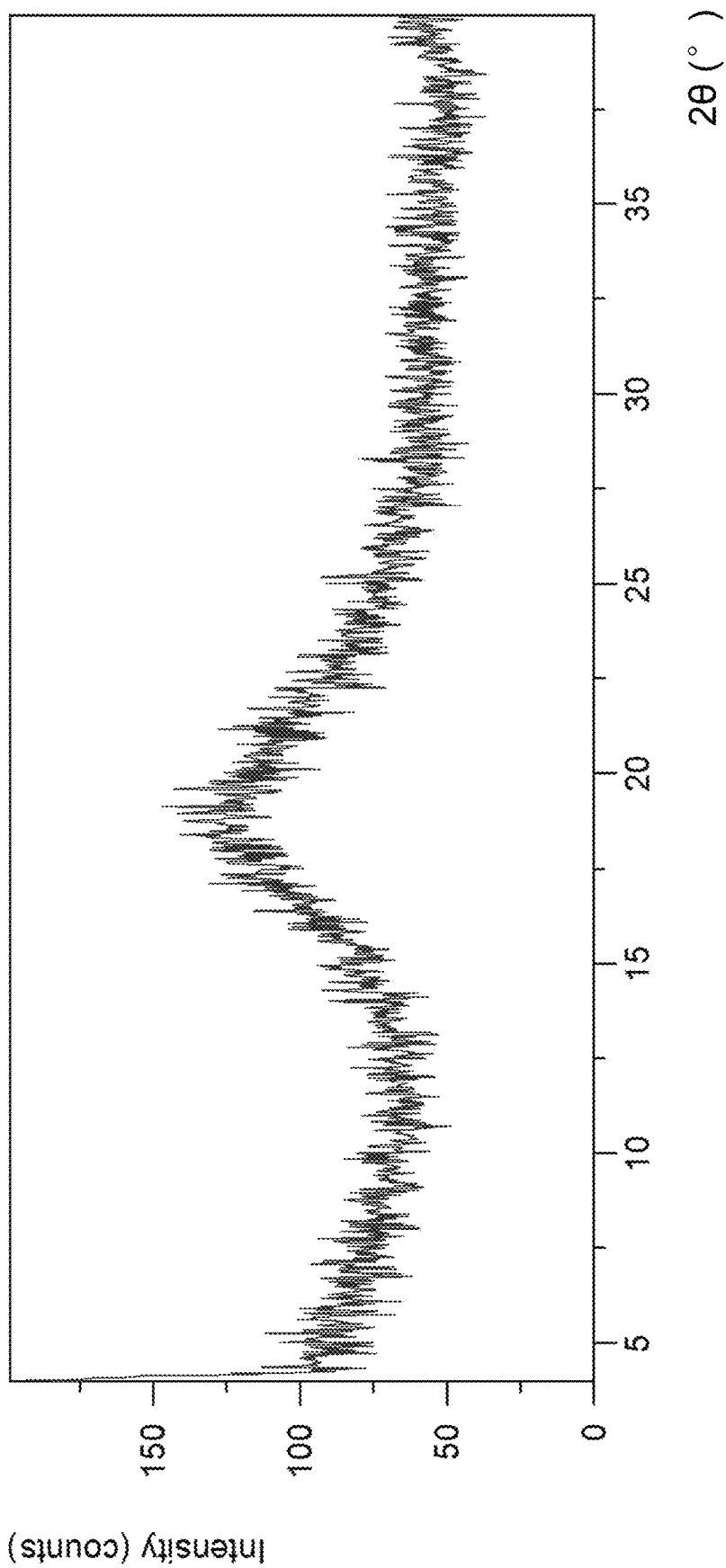
FIG. 10 is an XRPD pattern of prior art Solid B according to some embodiments of the present disclosure.

Prior art Solid B was obtained after repeating prior art P2, and an XRPD pattern is shown in FIG. 10.

Example 8: Solvent Residue of Form CSI, Form CSII and Prior Art Solids

Figure 11:
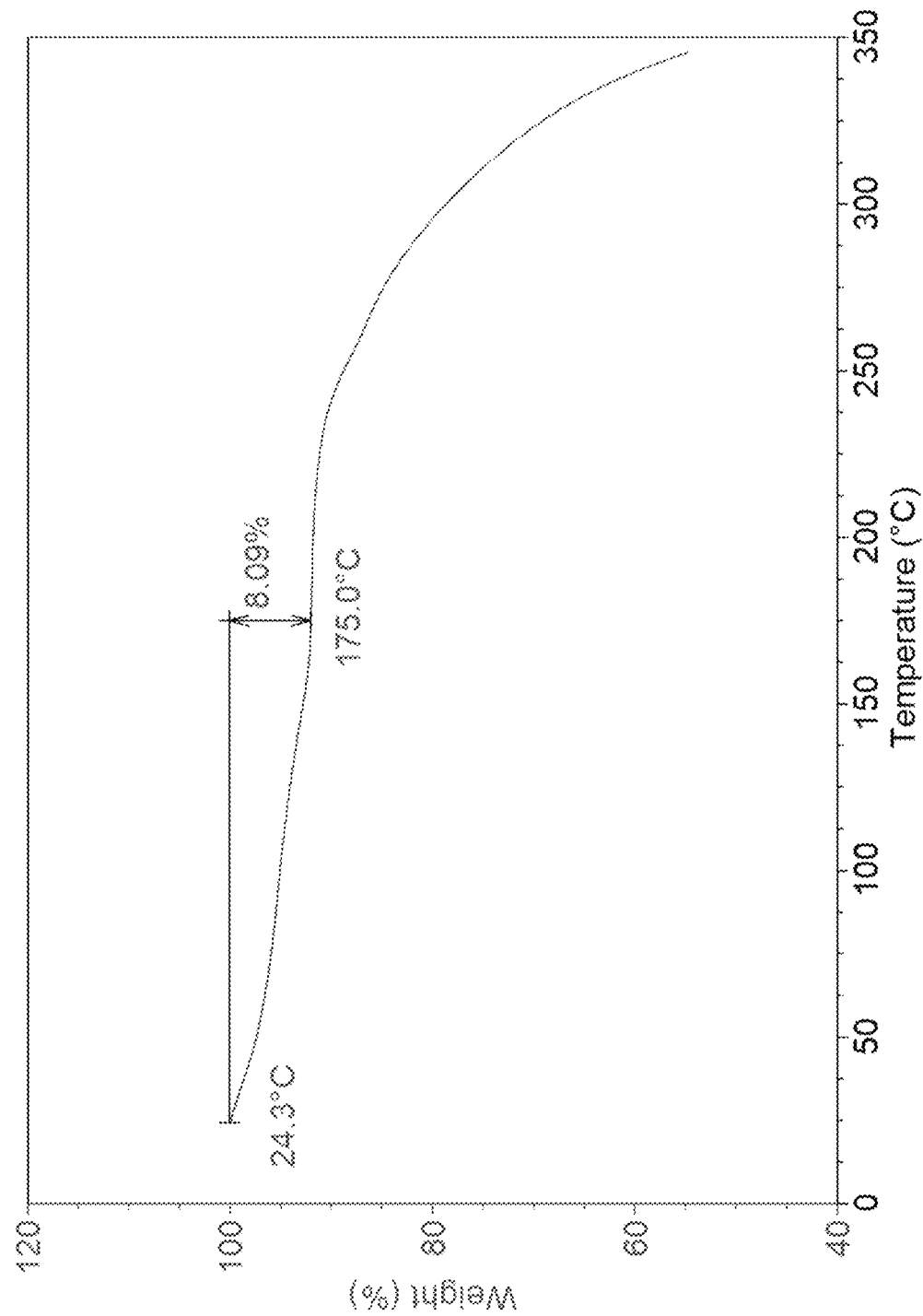
FIG. 11 is a TGA curve of the prior art Solid A according to some embodiments of the present disclosure.

Form CSI and Form CSII have almost no residual solvent according to the TGA curves. A TGA curve of prior art Solid A is shown in FIG. 11, which shows a weight loss of 8.1% up to 175° C. Furthermore, residual solvent of prior art Solid A was tested by GC. The results show that it has 38 ppm of residual methanol and 4853 ppm of residual 1,4-dioxane.

Example 9: Purity of Form CSI, Form CSII and Prior Art Solids

Purity of Form CSI, Form CSII and prior art solids were tested, and the results are listed in Table 6.

The results show that purity of Form CSI and Form CSII are higher than that of prior art solids.

TABLE 6

| Sample | Prior art Solid A | Prior art Solid B | Form CSI | Form CSII |
|---|---|---|---|---|
| Purity | 98.77% | 98.87% | 99.50% | 99.30% |

Example 10: Humidity Stability of Form CSI, Form CSII and Prior Art Solids

Figure 12:
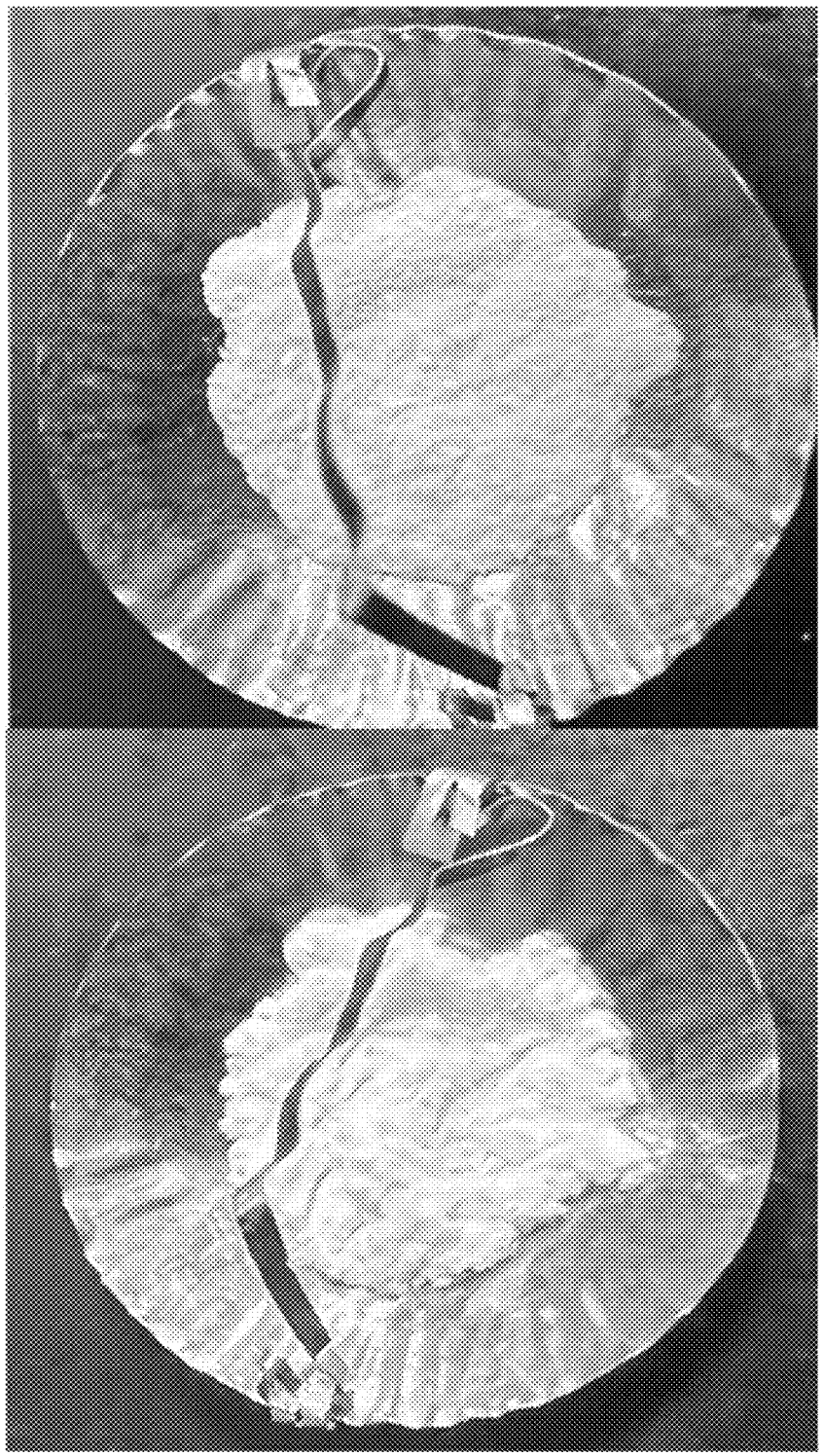
FIG. 12 is images of sample appearances of the Form CSI before and after humidity stability test according to some embodiments of the present disclosure (left: before test, right: after test)
Figure 13:
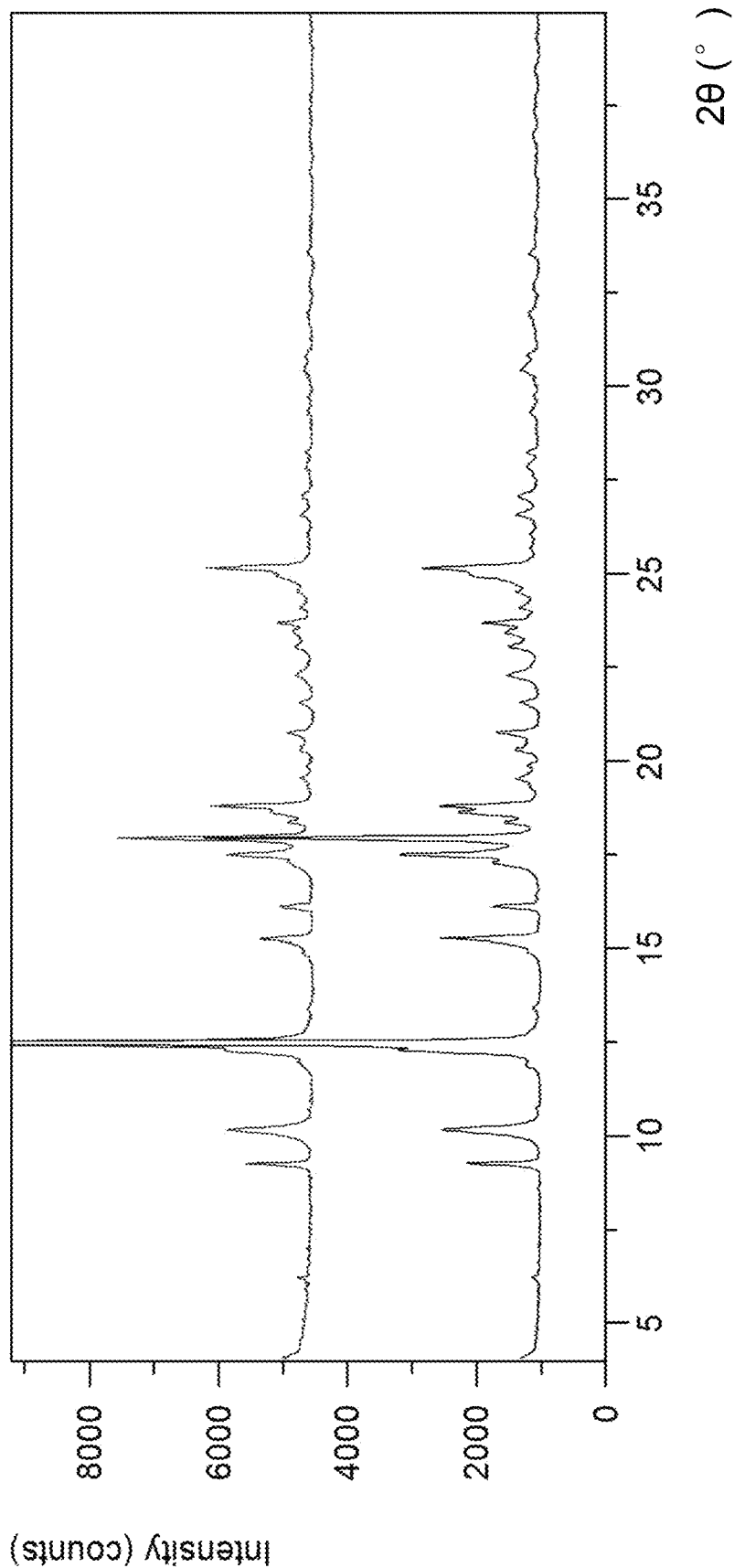
FIG. 13 is an XRPD pattern overlay of the Form CSI before and after humidity stability test according to some embodiments of the present disclosure (top: before test, bottom: after test)
Figure 14:
FIG. 14 is images of sample appearances of the Form CSII before and after humidity stability test according to some embodiments of the present disclosure (left: before test, right: after test)
Figure 15:
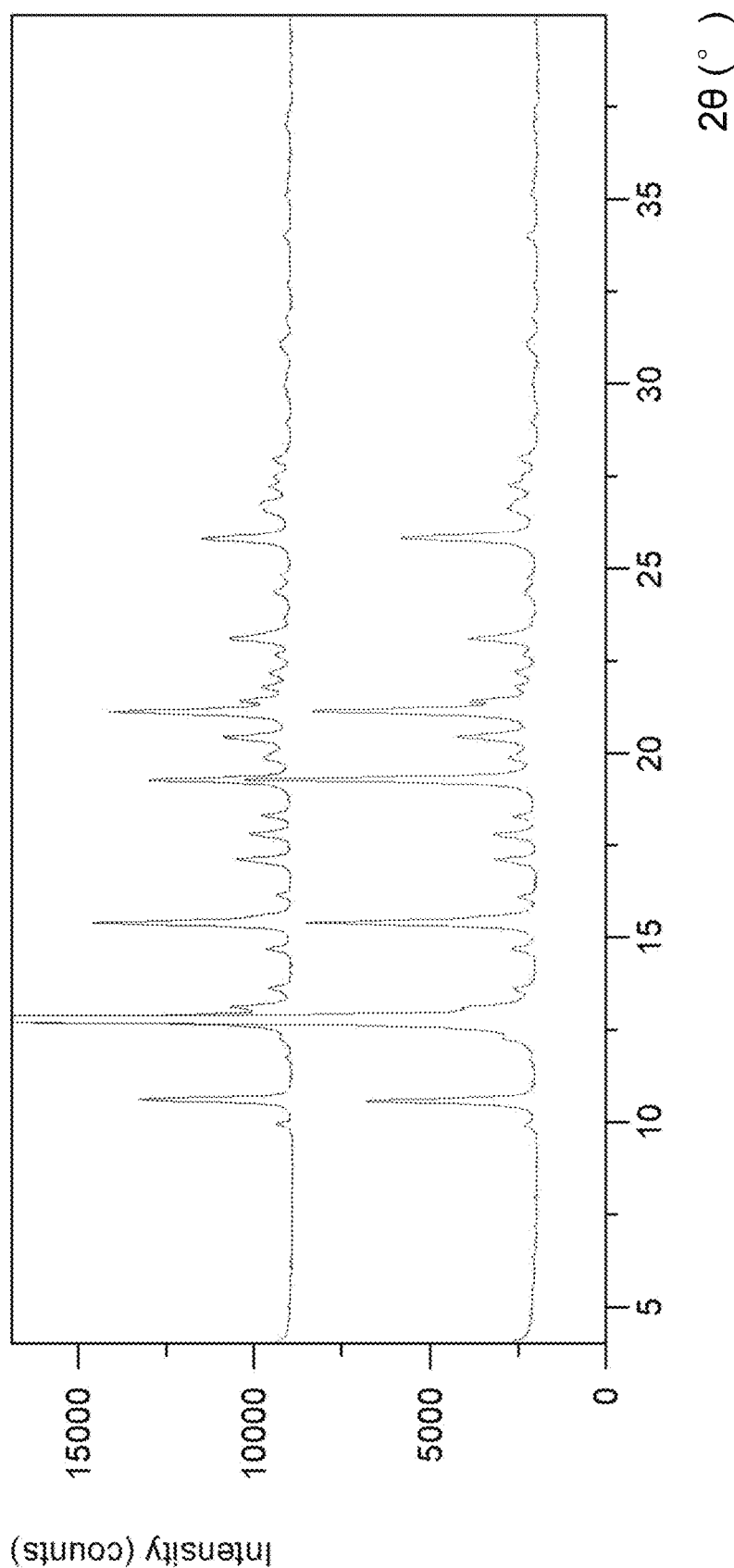
FIG. 15 is an XRPD pattern overlay of the Form CSII before and after humidity stability test according to some embodiments of the present disclosure (top: before test, bottom: after test)
Figure 16:
FIG. 16 is images of sample appearances of the prior art Solid A before and after humidity stability test according to some embodiments of the present disclosure (left: before test, right: after test)
Figure 17:
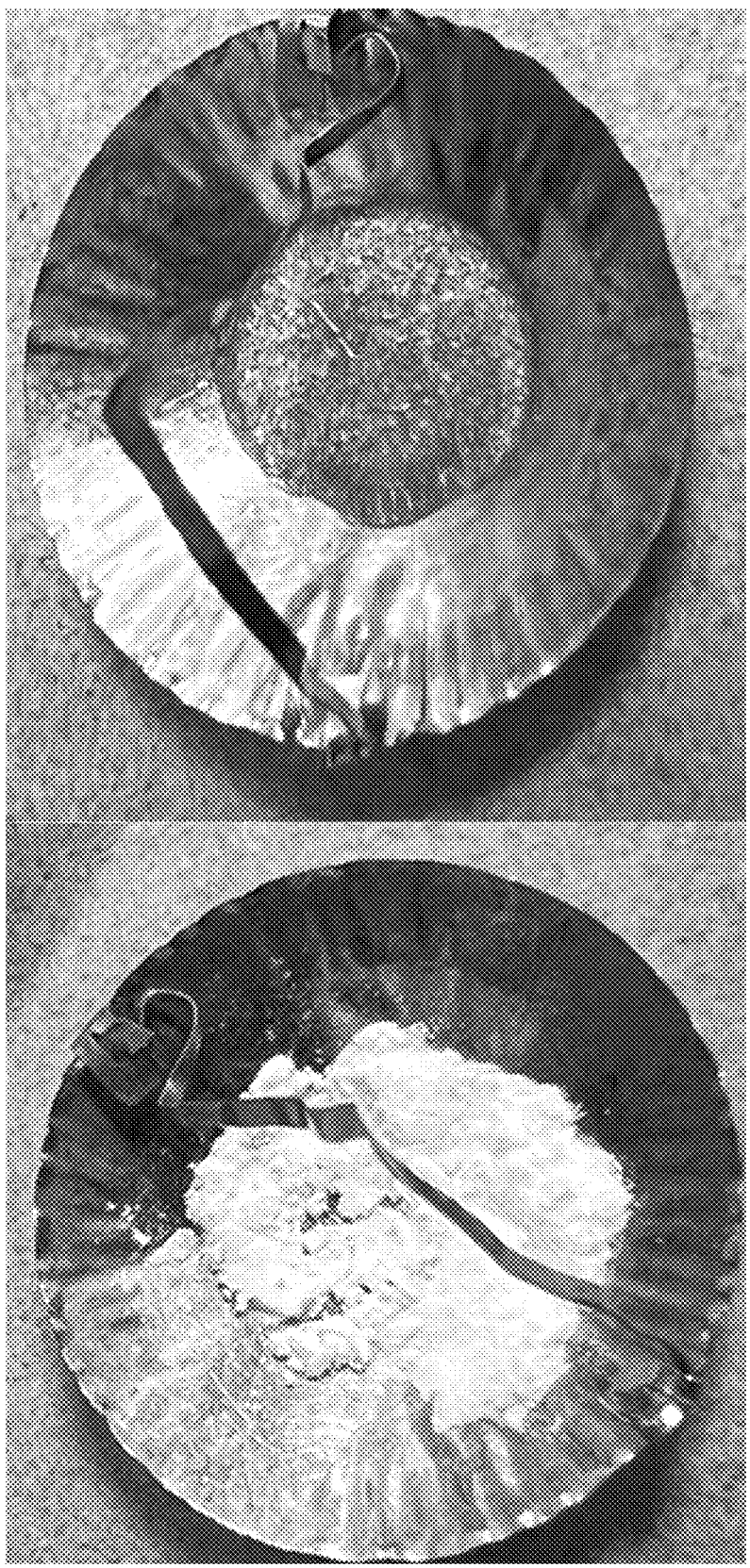
FIG. 17 is images of sample appearances of the prior art Solid B before and after humidity stability test according to some embodiments of the present disclosure (left: before test, right: after test)

DVS analyzer was applied to evaluate the humidity stability of prior art solids, Form CSI and Form CSII. The results are listed in Table 7. The appearance of Form CSI before and after humidity stability test is shown in FIG. 12, and an XRPD pattern of Form CSI before and after test is shown in FIG. 13. The appearance of Form CSII before and after humidity stability test is shown in FIG. 14, and an XRPD pattern of Form CSII before and after test is shown in FIG. 15. The appearance of prior art Solid A and prior art Solid B before and after humidity stability test are shown in FIG. 16 and FIG. 17.

TABLE 7

| Form | Condition | Appearance after test |
|---|---|---|
| Prior art Solid A | 0% RH-95% RH | Transparent solid |
| Prior art Solid B | 0% RH-95% RH | Transparent solid |
| Form CSI | 0% RH-95% RH | Powder |
| Form CSII | 0% RH-95% RH | Powder |

The results show that no obvious change of appearance and no crystal change are observed for Form CSI and Form CSII before and after humidity stability test. Prior art Solid A and Solid B change to transparent solids after humidity stability test. The humidity stability of Form CSI and Form CSII is superior to that of prior art solids. Prior art solids deliquesce under high humidity.

Example 11: Stability of Form CSI and Solids in the Prior Art

Figure 18:
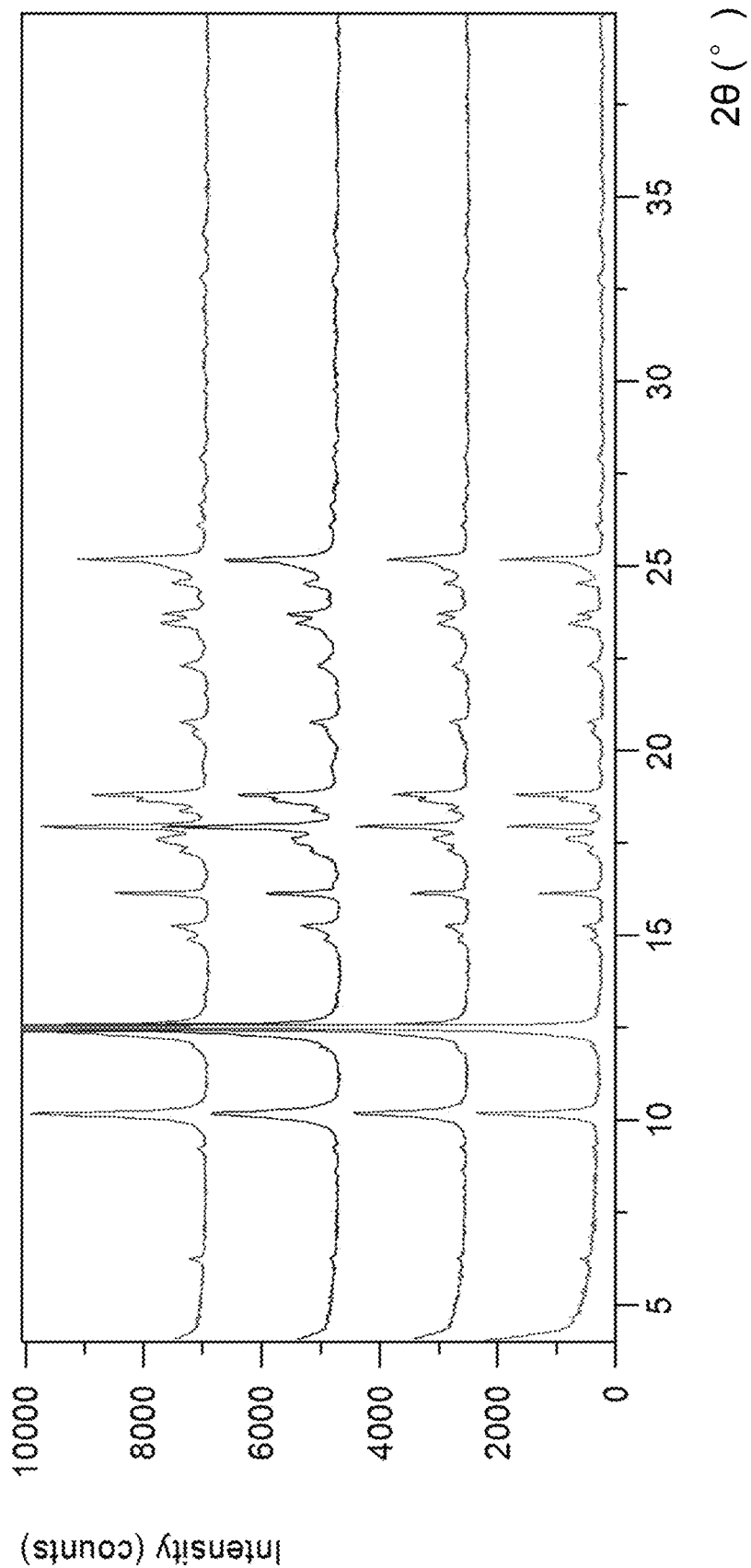
FIG. 18 is an XRPD pattern overlay of the Form CSI before and after storage under different conditions with open package according to some embodiments of the present disclosure (from bottom to top: initial, 25° C./60% RH for 6 months with open package, 40° C./75% RH for 6 months with open package, 60° C./75% RH for 3 months with open package)
Figure 19:
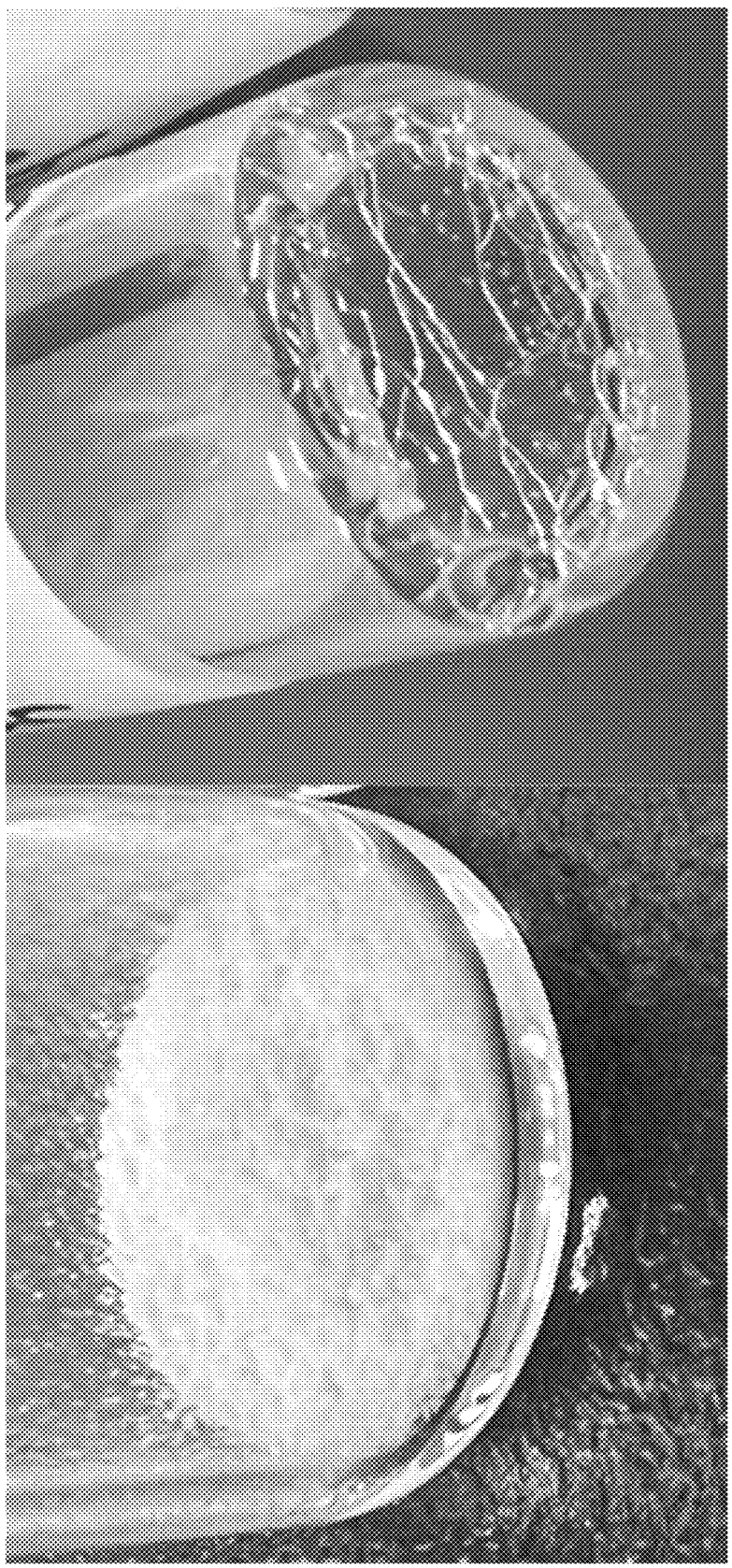
FIG. 19 is images of sample appearances of the prior art Solid A before and after storage under 60° C./75% RH with open package for one week according to some embodiments of the present disclosure (left: before storage, right: after storage)
Figure 20:
FIG. 20 is images of sample appearances of the prior art Solid B before and after storage under 60° C./75% RH with open package for one week according to some embodiments of the present disclosure (left: before storage, right: after storage)

An appropriate amount of Form CSI was packaged with corresponding condition, and then stored with open package under 25° C./60% RH, 40° C./75% RH and 60° C./75% RH conditions for a period. Appropriate amounts of prior art solids were packaged with corresponding condition, and then stored with open package under 25° C./60% RH and 60° C./75% RH conditions for a period. Chemical purity and crystalline form were checked by HPLC and XRPD, respectively. The results are shown in Table 8. An XRPD pattern overlay of Form CSI before and after storage is shown in FIG. 18. The appearance comparison of prior art solid A and Solid B before and after storage are shown in FIG. 19 and FIG. 20, respectively.

TABLE 8

| Initial Form | Condition | Packing Condition | Time | Form | Appearance | Purity |
|---|---|---|---|---|---|---|
| Prior art Solid A | Initial | — | — | Amorphous | Powder | 98.77% |
|  | 25° C./60% RH | Open | 1 month | Amorphous | Powder | 98.65% |
|  | 60° C./75% RH | Open | 1 week | Gel | Gel | — |
| Prior art Solid B | Initial | — | — | Amorphous | Powder | 98.87% |
|  | 25° C./60% RH | Open | 1 month | Amorphous | Powder | 98.73% |
|  | 60° C./75% RH | Open | 1 week | Gel | Gel | — |
| Form CSI | Initial | — | — | Form CSI | Powder | 99.50% |
|  | 25°C/60% RH | Open | 6 months | Form CSI | Powder | 99.45% |
|  | 40°C/75% RH | Open | 6 months | Form CSI | Powder | 99.45% |
|  | 60°C/75% RH | Open | 3 months | Form CSI | Powder | — |

Open: Put the sample into a glass vial, cover the vial with aluminum foil, and punch 5-10 holes in the foil.

The results show that the purity of both prior art solid A and Solid B decrease after stored under 25° C./60% RH open condition for one month, and the samples become into gel after stored under 60° C./75% RH open condition for one week. Form CSI is stable for at least 6 months under 25° C./60% RH and 40° C./75% RH open conditions, and at least 3 months at 60° C./75% RH open condition. Form CSI has better physicochemical stability under long-term, accelerated and stress conditions.

Example 12: Stability of Form CSI Upon Mechanical Force

Figure 21:
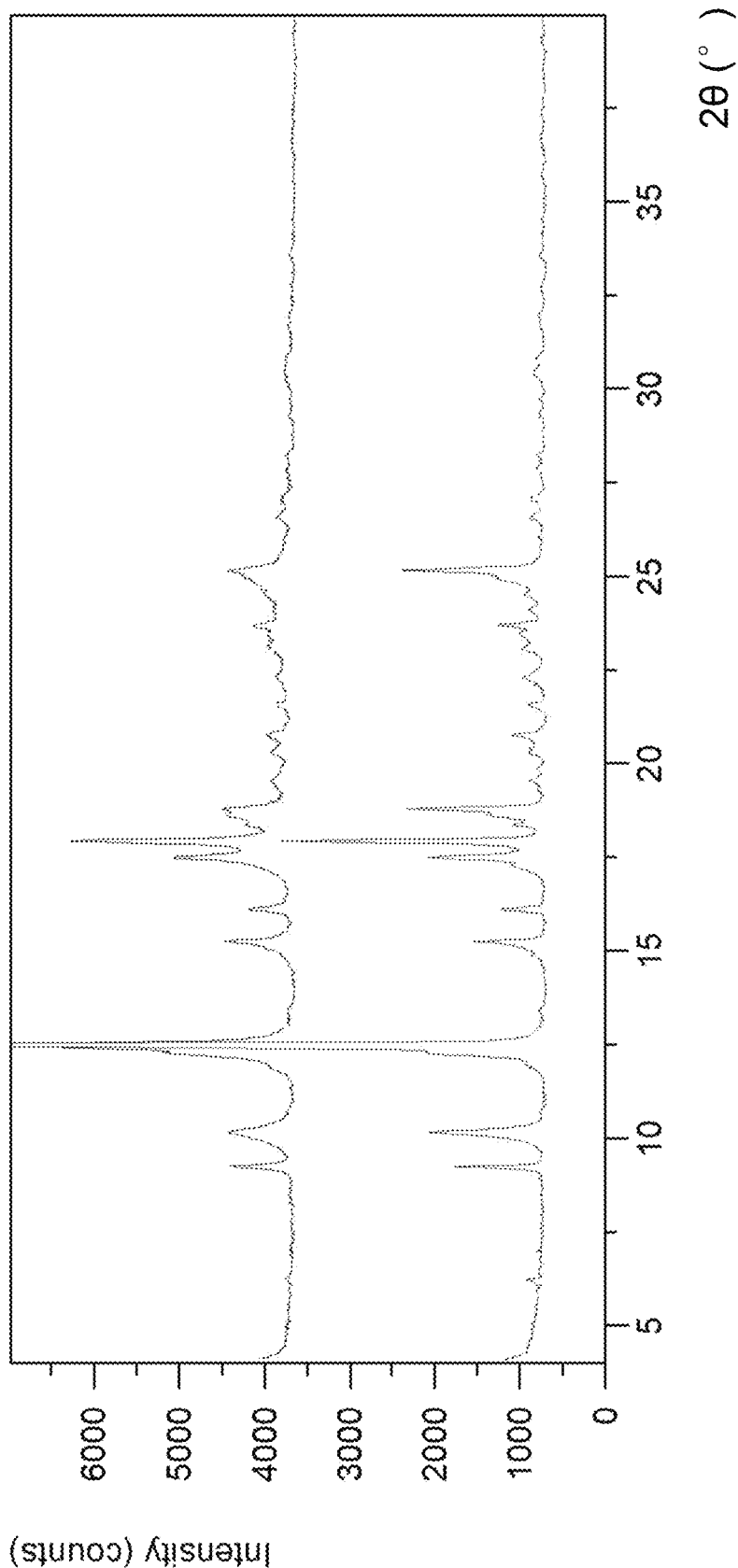
FIG. 21 is an XRPD pattern overlay of the Form CSI before and after ball milling according to some embodiments of the present disclosure (top: before ball milling, bottom: after ball milling)

Form CSI was milled for 5 min at a vibration speed of 500 rpm in a ball mill. The sample before and after ball milling were checked by XRPD. The test result is shown in FIG. 21. No crystal change is observed for the Form CSI.

Figure 22:
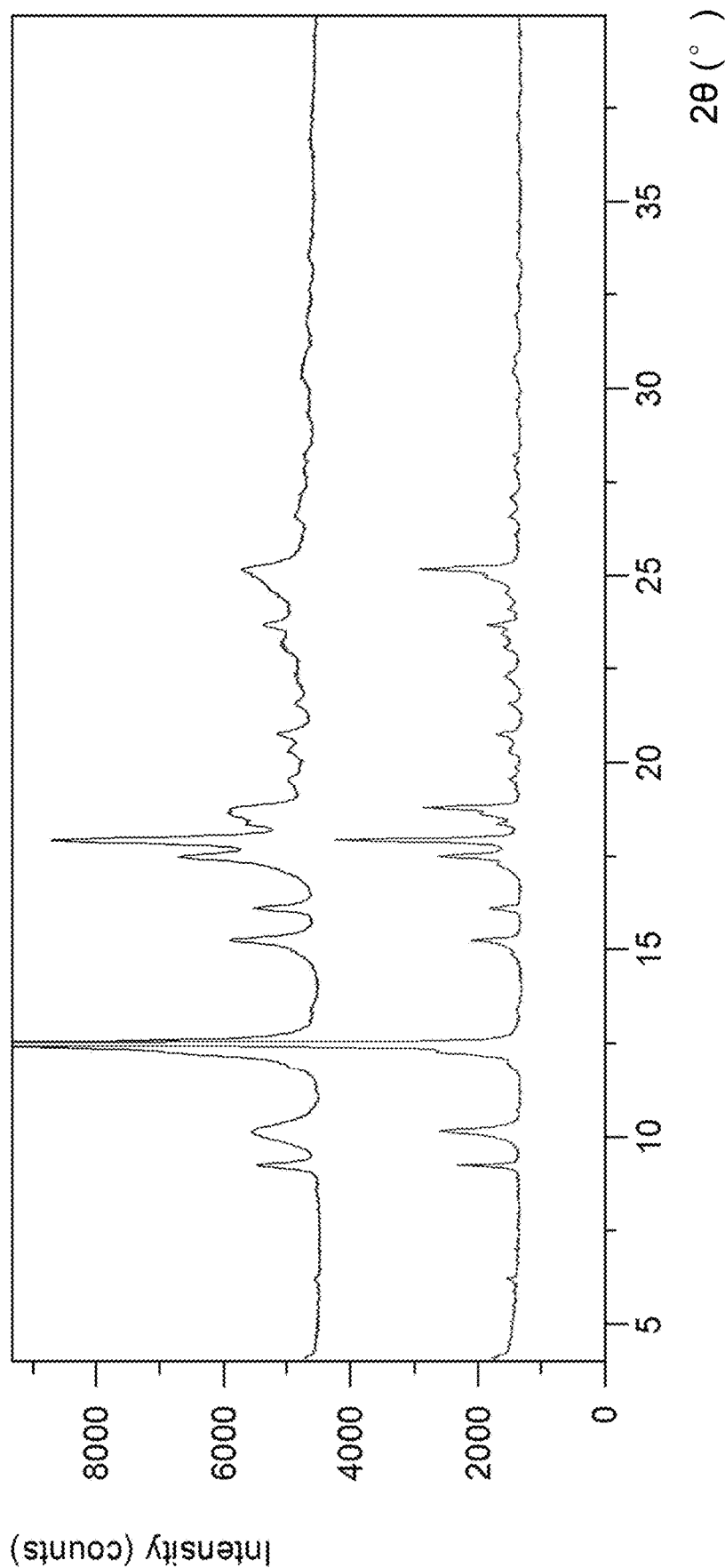
FIG. 22 is an XRPD pattern overlay of the Form CSI before and after tableting according to some embodiments of the present disclosure (top: after tableting, bottom: before tableting)

An appropriate amount of Form CSI was compressed into a tablet using a manual tablet press under a pressure of 20 kN with a φ6 mm round tooling. Crystalline form before and after tableting were checked by XRPD. The test result is shown in FIG. 22. The Form CSI keeps stable after tableting.

The results show that Form CSI has good stability under mechanical force.

Example 13: Hygroscopicity of Form CSI

Figure 23:
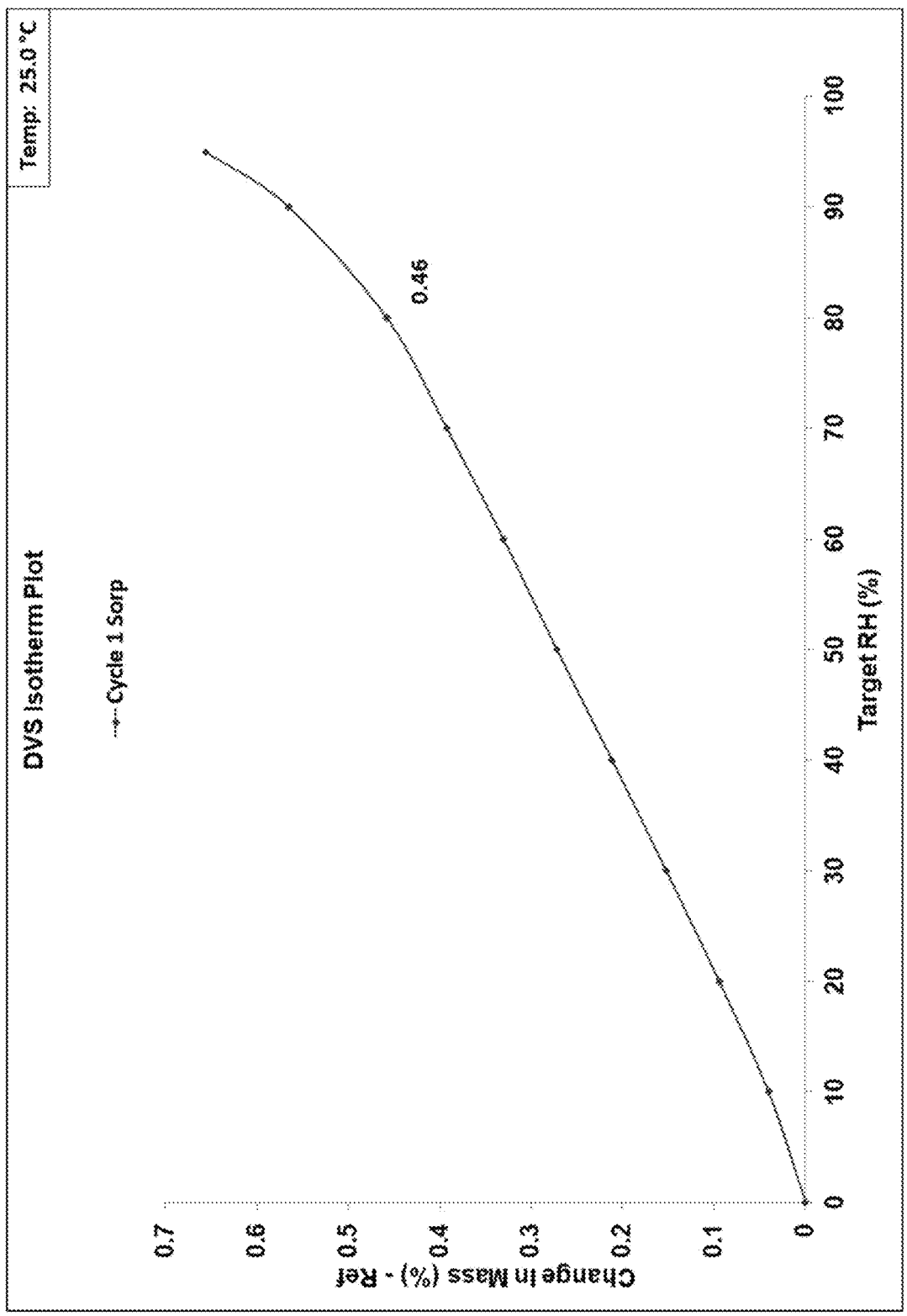
FIG. 23 is a DVS curve of the Form CSI according to some embodiments of the present disclosure.

DVS analyzer was applied to evaluate the hygroscopicity of Form CSI with about 10 mg of sample. A DVS curve of the Form CSI is shown in FIG. 23, and the result shows that the weight gain of the Form CSI from 0% RH to 80% RH is 0.46%.

Example 14: Preparation of CSI Drug Product

Figure 24:
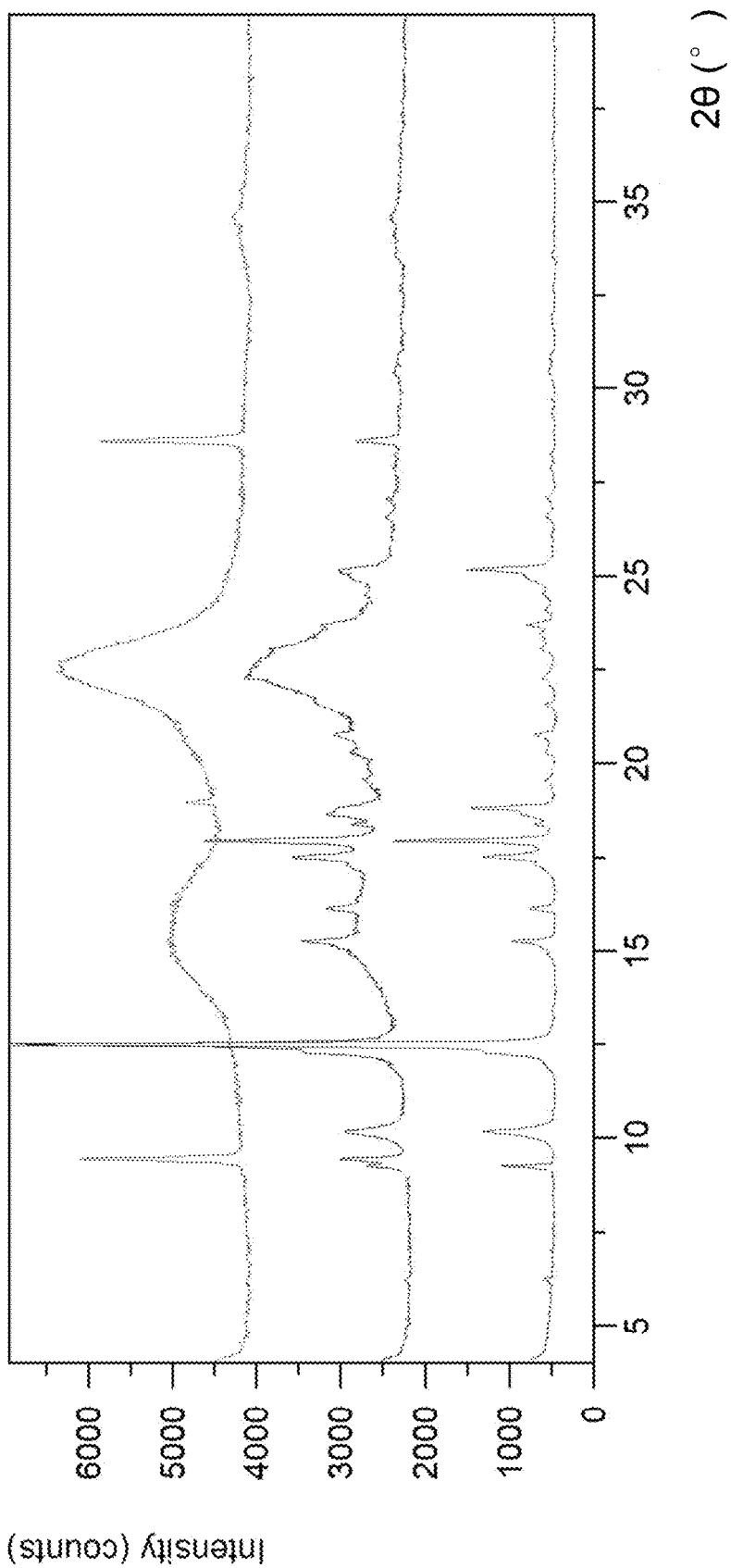
FIG. 24 is an XRPD pattern overlay of the Form CSI and formulation thereof according to some embodiments of the present disclosure (from bottom to top: Form CSI drug substance, Form CSI drug product, excipients)

Form CSI drug product was prepared by using the formulation as shown in Table 9 and preparation process as shown in Table 10. Blank prescription was shown in Table 11. An XRPD of blank prescription (excipients) and the samples before and after the formulation were tested, and result is shown in FIG. 24. The result shows that Form CSI keeps stable before and after the formulation process.

TABLE 9

| No. | Composition | % (w/w) | mg/tablet |
| --- | --- | --- | --- |
| 1 | Compound I | 30.0 | 30.0 |
| 2 | Microcrystalline Cellulose | 59.5 | 59.5 |
| 3 | Hydroxypropyl Methyl Cellulose | 3.0 | 3.0 |
| 4 | Crospovidone | 6.0 | 6.0 |
| 5 | Colloidal Silicon Dioxide | 0.5 | 0.5 |
| 6 | Talcum Powder | 1.0 | 1.0 |
| | Total | | 100 |

TABLE 10

| Stage | Procedure |
| --- | --- |
| Pre-blending | According to the formulation, materials No. 1-6 were weighed into a glass vial and blended for 30 min manually. |
| Simulation of dry granulation | The mixture was pressed by a single punch manual tablet press (type: ENERPAC; die: q20 mm round; flake weight: 500 mg ± 100 mg; pressure: 10 ± 1 kN). The flakes were pulverized and sieved through a 20-mesh sieve to obtain final granules. |
| Tableting | Fill the final granules into 2# capsules (about 100 mg/capsule). |
| Packaging | One capsule with 1 g of desiccant was placed into a 35 cc HDPE bottle, and then the bottle was sealed. |

TABLE 11

| | Blank Prescription | % (w/w) |
| --- | --- | --- |
| 1 | Microcrystalline Cellulose | 85.0 |
| 2 | Hydroxypropyl Methyl Cellulose | 4.3 |
| 3 | Crospovidone | 8.6 |

TABLE 11-continued

| | Blank Prescription | % (w/w) |
| --- | --- | --- |
| 4 | Colloidal Silicon Dioxide | 0.7 |
| 5 | Talcum powder | 1.4 |
| | Total | 100.0 |

Example 15: Stability of Form CSI Drug Product

Figure 25:
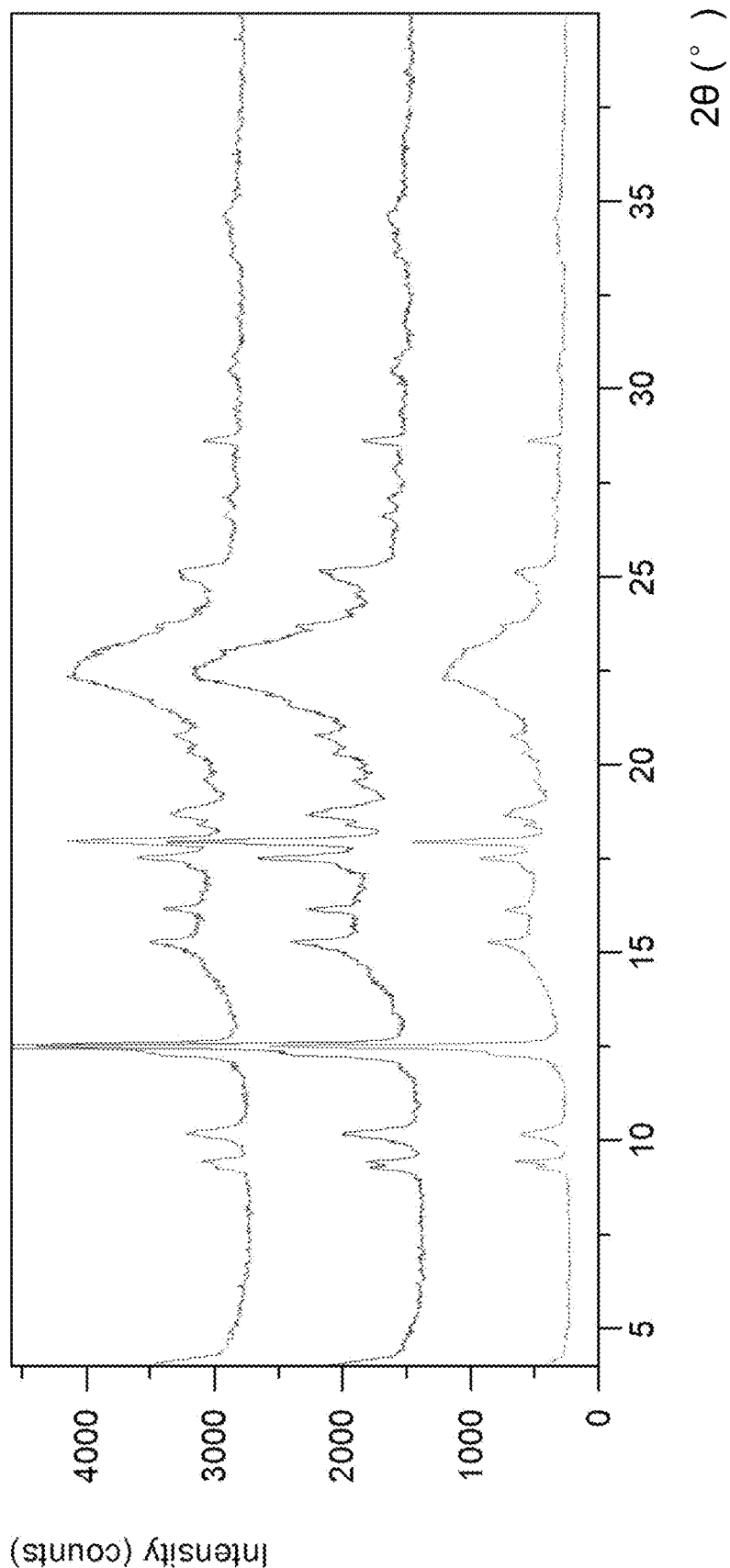
FIG. 25 is an XRPD pattern overlay of the Form CSI drug product before and after storage under different conditions according to some embodiments of the present disclosure (from bottom to top: initial, 25° C./60% RH for one month with desiccant and sealed package, 40° C./75% RH for one month with desiccant and sealed package)

Form CSI drug products using sealed package with desiccant were stored under 25° C./60% RH and 40° C./75% RH conditions. Chemical purity and crystalline form were checked by HPLC and XRPD, respectively. The results are shown in Table 12, and an XRPD pattern overlay before and after storage is shown in FIG. 25. The results indicate that Form CSI drug product keeps stable for at least 1 month under 25° C./60% RH and 40° C./75% RH sealed with desiccant, and the purity has almost no change.

TABLE 12

| Condition | Packing Condition | Time | Form | Purity Change |
| --- | --- | --- | --- | --- |
| 25° C./60% RH | Sealed with desiccant | 1 month | Form CSI | 0 |
| 40° C./75% RH | Sealed with desiccant | 1 month | Form CSI | 0.05% |

Example 16: Stability of Form CSII and Solids in the Prior Art

Figure 26:
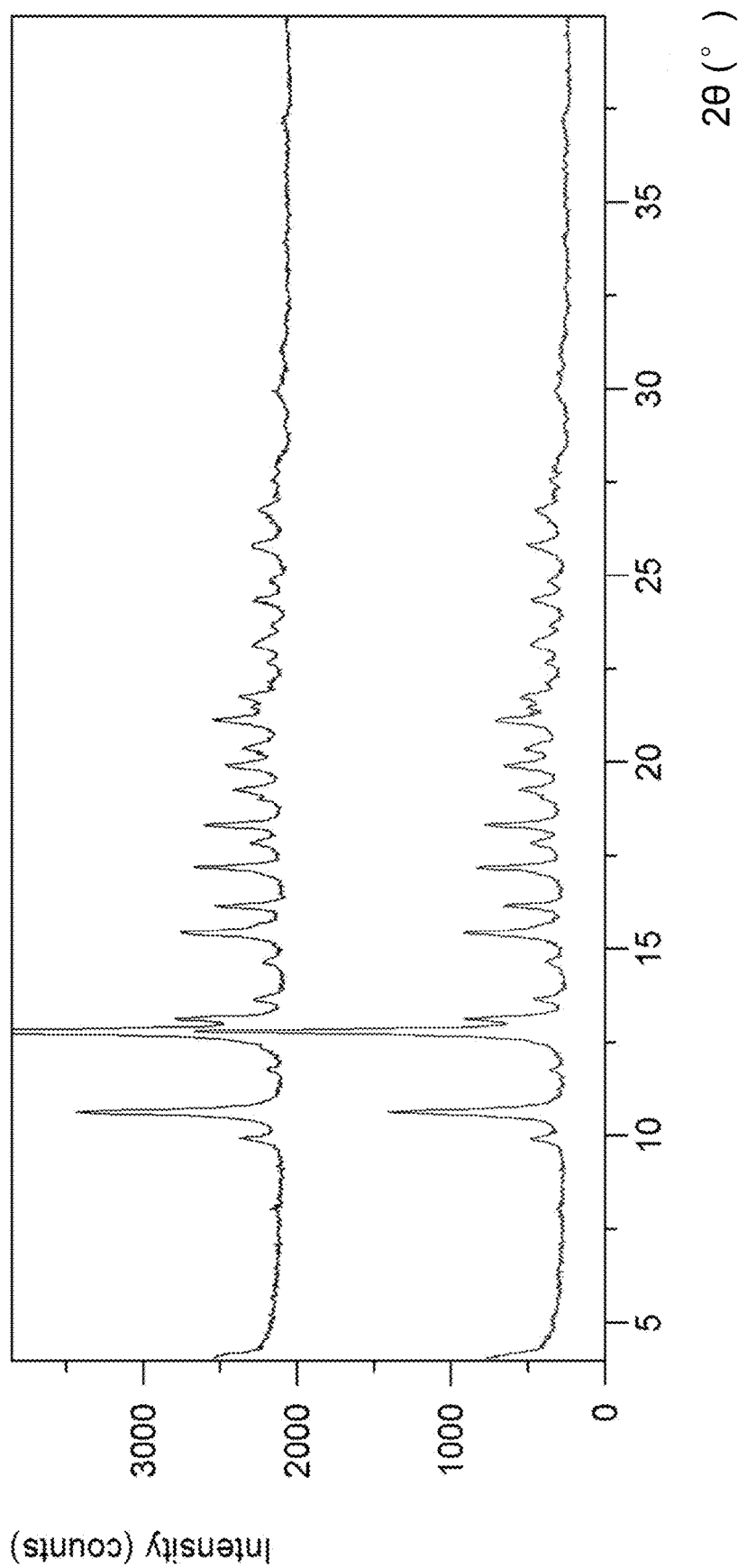
FIG. 26 is an XRPD pattern overlay of the Form CSII before and after storage under 60° C./75% RH with open package for 4 weeks according to some embodiments of the present disclosure (top: after storage, bottom: before storage)

An appropriate amount of Form CSII and prior art solids were packaged with corresponding conditions, and then stored with open package under 25° C./60% RH and 60° C./75% RH for a period. Chemical purity and crystalline form were checked by HPLC and XRPD, respectively. The results are shown in Table 13. An XRPD pattern overlay of Form CSII before and after storage is shown in FIG. 26. The appearance comparison of prior art solid A and Solid B before and after storage are shown in FIG. 19 and FIG. 20, respectively.

TABLE 13

| Initial Form | Condition | Time | Form | Appearance |
| --- | --- | --- | --- | --- |
| Prior art Solid A | Initial | — | — | Amorphous Gel | Powder Gel |
| | 60° C./75% RH Open | 1 week | | |
| Prior art Solid B | Initial | — | — | Amorphous Gel | Powder Gel |
| | 60° C./75% RH Open | 1 week | | |
| Form CSII | Initial | — | — | Form CSII | Powder |
| | 60° C./75% RH Open | 4 weeks | Form CSII | Powder |

The results show that Form CSII keeps physically stable for at least four weeks under 60° C./75% RH open condition. Prior art Solid A and Solid B become into gel after stored at 60° C./75% RH open condition for one week.

Example 17: Stability of Form CSII Upon Mechanical Force

Form CSII was milled for 5 min at a vibration speed of 500 rpm in a ball mill. The sample before and after ball milling were checked by XRPD. The test result shows that the Form CSII keeps stable after ball milling.

An appropriate amount of Form CSII was compressed into a tablet using a manual tablet press under a pressure of 20 kN with a @6 mm round tooling. Crystalline form before and after tableting were checked by XRPD. Form CSII kept stable after tableting. The results show that Form CSII has good stability under mechanical force.

Example 18: Hygroscopicity of Form CSII

Figure 27:
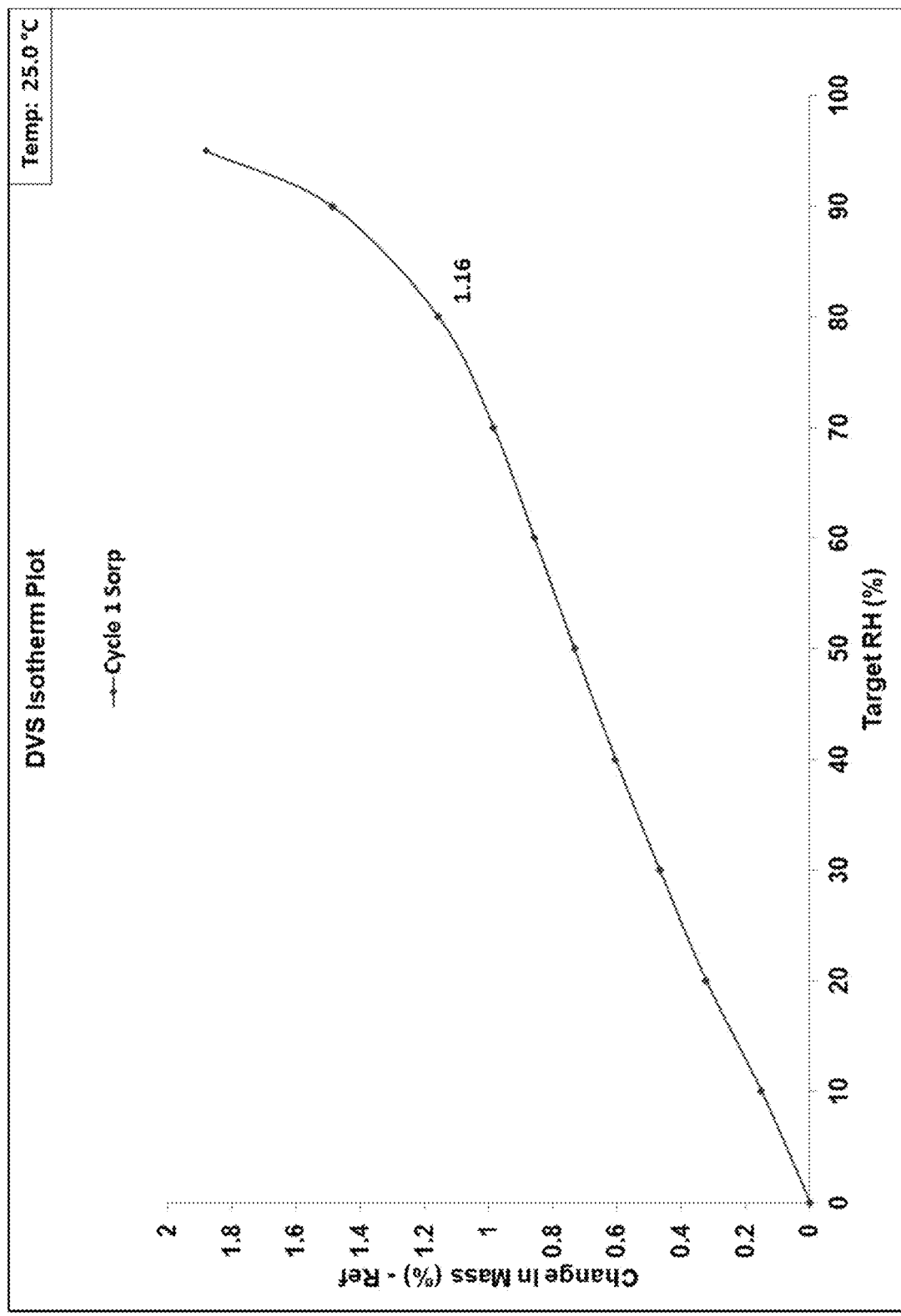
FIG. 27 is a DVS curve of the Form CSII according to some embodiments of the present disclosure.

DVS analyzer was applied to evaluate the hygroscopicity of Form CSII with about 10 mg of sample. A DVS curve of Form CSII is shown in FIG. 27, and the result shows that the weight gain of Form CSII from 0% RH to 80% RH is 1.16%.

Example 19: Preparation of CSII Drug Product

Figure 28:
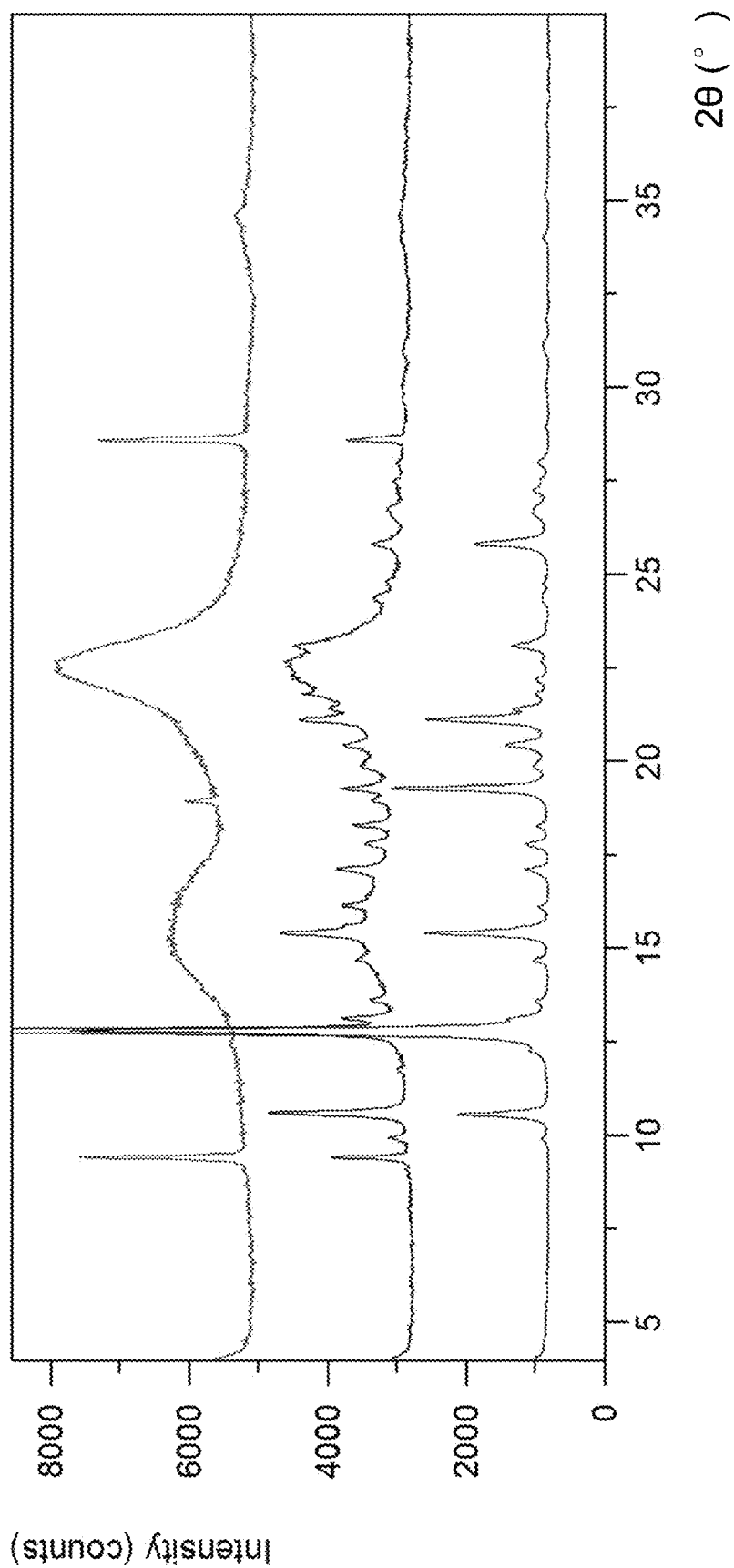
FIG. 28 is an XRPD pattern overlay of the Form CSII and formulation thereof according to some embodiments of the present disclosure (from bottom to top: Form CSII drug substance, Form CSII drug product, excipients)

Form CSII drug product was prepared by using the formulation as shown in Table 9 and preparation process as shown in Table 10. Blank prescription was shown in Table 11. An XRPD of Blank prescription (excipients) and Form CSII before and after the formulation were tested, and result is shown in FIG. 28. The result shows that Form CSII keeps stable before and after the formulation process.

Example 20: Stability of Form CSII in Drug Product

Figure 29:
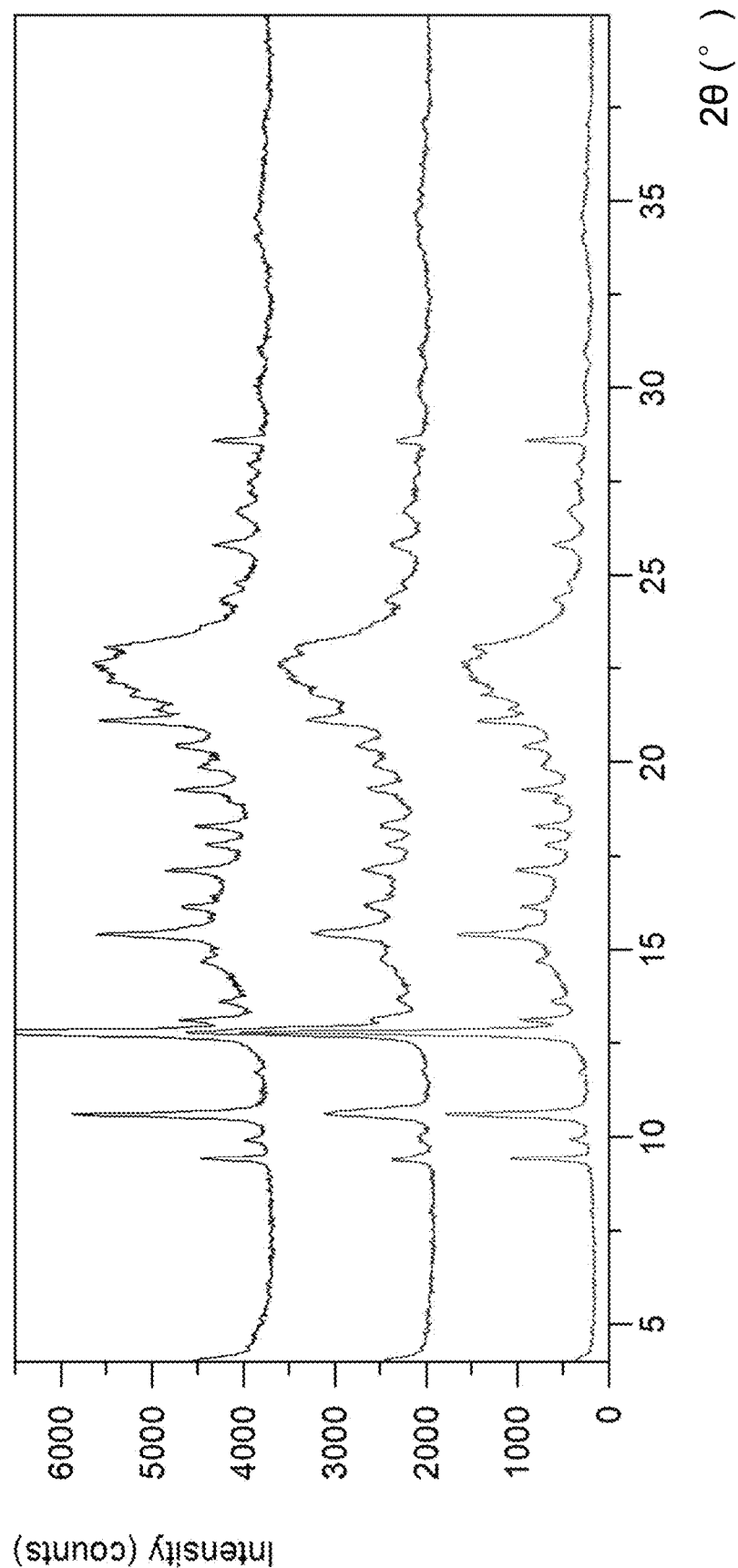
FIG. 29 is an XRPD pattern overlay of the Form CSII drug product before and after storage under different conditions according to some embodiments of the present disclosure (from bottom to top: initial, 25° C./60% RH for one month with desiccant and sealed package, 40° C./75% RH for one month with desiccant and sealed package).

Form CSII drug products using sealed package with desiccant were stored under 25° C./60% RH and 40° C./75% RH conditions. Chemical purity and crystalline form were checked by HPLC and XRPD, respectively. The results are shown in Table 14, and an XRPD pattern overlay of Form CSII drug product before and after storage is shown in FIG. 29. The results indicate that Form CSII drug product keeps stable for at least 1 month under 25° C./60% RH and 40° C./75% RH sealed with desiccant conditions, and the purity has almost no change.

TABLE 14

| Condition | Packing Condition | Time | Form | Purity Change |
|---|---|---|---|---|
| 25° C./60% RH | Sealed with desiccant | 1 month | Form CSII | 0 |
| 40° C./75% RH | Sealed with desiccant | 1 month | Form CSII | 0.03% |

The examples described above are only for illustrating the technical concepts and features of the present disclosure, and intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure.

What is claimed is:

1. A crystalline form of (5S,8S,10aR)—N-benzhydryl-5-((S)-2-(methylamino)propanamido)-3-(3-methylbutanoyl)-6-oxodecahydropyrrolo[1,2-a][1,5]diazocine-8-carboxamide (Compound I):

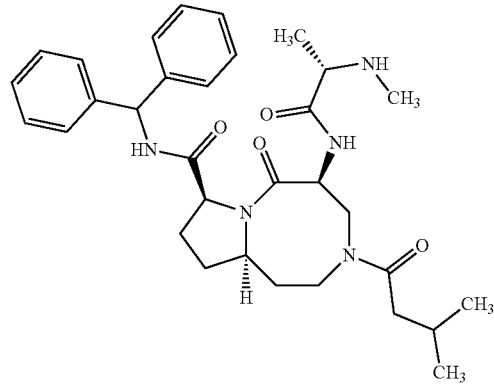

Compound I (i) wherein the crystalline form is Form CSI; and
wherein Form CSI is characterized by an X-ray powder diffraction pattern comprising at least one characteristic peak at an angle (° 2θ) selected from the group consisting of 10.2°±0.2° 2θ, 12.5°±0.2° 2θ, and 18.0°±0.2° 2θ; or
(ii) wherein the crystalline form is Form CSII; and
wherein Form CSII is characterized by an X-ray powder diffraction pattern comprising at least one characteristic peak at an angle (° 2θ) selected from the group consisting of 10.6°±0.2° 2θ, 12.8°±0.2° 2θ, and 14.7°±0.2° 2θ.

2. The crystalline form according to claim 1, wherein the crystalline form is further characterized by an X-ray powder diffraction pattern comprising at least two characteristic peaks at angles (° 2θ) selected from the group consisting of 10.2°±0.2° 2θ, 12.5°±0.2° 2θ, and 18.0°±0.2° 2θ.

3. The crystalline form according to claim 2, wherein the crystalline form is further characterized by an X-ray powder diffraction pattern comprising one, two, or three additional characteristic peaks at angles (° 2θ) selected from the group consisting of 9.3°±0.2° 2θ, 15.3°±0.2° 2θ, and 25.2°±0.2° 2θ.

4. The crystalline form according to claim 2, wherein the crystalline form is further characterized by an X-ray powder diffraction pattern as shown in FIG. 1 or FIG. 4.

5. The crystalline form according to claim 1, wherein the crystalline form is further characterized by an X-ray powder diffraction pattern comprising at least two characteristic peaks at angles (° 2θ) selected from the group consisting of 10.6°±0.2° 2θ, 12.8°±0.2° 2θ, and 14.7°±0.2° 2θ.

6. The crystalline form according to claim 5, wherein the crystalline form is further characterized by an X-ray powder diffraction pattern comprising one or two additional characteristic peaks at angles (° 2θ) selected from the group consisting of 9.9°±0.2° 2θ and 16.2°±0.2° 2θ.

7. The crystalline form according to claim 5, wherein the crystalline form is further characterized by an X-ray powder diffraction pattern comprising one, two, or three additional characteristic peaks at angles (° 2θ) selected from the group consisting of 17.2°±0.2° 2θ, 17.9°±0.2° 2θ, and 18.3°±0.2° 2θ.

8. The crystalline form according to claim 5, wherein the crystalline form is further characterized by an X-ray powder diffraction pattern as shown in FIG. 5, FIG. 6, or FIG. 7.

9. A pharmaceutical composition comprising one or more pharmaceutically acceptable excipients and a therapeutically effective amount of the crystalline form according to claim 1.

10. A method for treating locally advanced squamous cell carcinoma of the head and neck (LA SCCHN) in a subject, wherein the method comprises administering to the subject in need thereof a therapeutically effective amount of the crystalline form according to claim 1.

* * * * *